US009827002B2

(12) United States Patent
Hausen et al.

(10) Patent No.: US 9,827,002 B2

(45) Date of Patent: Nov. 28, 2017

(54) TISSUE REMOVAL AND CLOSURE DEVICE

(71) Applicant: Dextera Surgical, Redwood City, CA (US)

(72) Inventors: Berrnard A. Hausen, Redwood City, CA (US); Brendan M. Donohoe, Fairfax, CA (US)

(73) Assignee: Dextera Surgical, Redwood City, CA (US)

( * ) Notice: Subject to any disclaimer, the term of this patent is extended or adjusted under 35 U.S.C. 154(b) by 0 days.

(21) Appl. No.: 15/161,693

(22) Filed: May 23, 2016

(65) Prior Publication Data

US 2016/0262750 A1 Sep. 15, 2016

Related U.S. Application Data

(63) Continuation-in-part of application No. 13/028,148, filed on Feb. 15, 2011.

(60) Provisional application No. 62/196,785, filed on Jul. 24, 2015.

(51) Int. Cl.

| | |
|---|---|
| ***A61B 17/068*** | (2006.01) |
| ***A61B 17/32*** | (2006.01) |
| *A61B 17/072* | (2006.01) |
| *A61B 17/00* | (2006.01) |
| *A61B 17/29* | (2006.01) |
| *A61B 90/00* | (2016.01) |

(52) U.S. Cl.

CPC ........ *A61B 17/32* (2013.01); *A61B 17/07207* (2013.01); *A61B 2017/00115* (2013.01); *A61B 2017/07214* (2013.01); *A61B 2017/07228* (2013.01); *A61B 2017/07278* (2013.01); *A61B 2017/07285* (2013.01); *A61B 2017/2927* (2013.01); *A61B 2017/2937* (2013.01); *A61B 2017/320052* (2013.01); *A61B 2090/0807* (2016.02)

(58) Field of Classification Search

CPC .... A61B 17/07207; A61B 2017/07214; A61B 2017/07285; A61B 2017/07271; A61B 2017/320052; A61B 2017/07228

See application file for complete search history.

(56) References Cited

U.S. PATENT DOCUMENTS

| | | | | |
|---|---|---|---|---|
| 5,868,760 A * | 2/1999 | McGuckin, Jr. | A61B 17/00234 | 227/179.1 |
| 6,264,086 B1 * | 7/2001 | McGuckin, Jr. | A61B 17/00234 | 227/175.1 |
| 7,128,253 B2 * | 10/2006 | Mastri | A61B 17/0684 | 227/176.1 |
| 7,207,471 B2 * | 4/2007 | Heinrich | A61B 17/072 | 227/175.1 |
| 7,235,089 B1 * | 6/2007 | McGuckin, Jr. | A61B 17/00234 | 227/180.1 |
| 7,438,209 B1 * | 10/2008 | Hess | A61B 17/0643 | 227/176.1 |

(Continued)

*Primary Examiner* — Andrew M Tecco

(74) *Attorney, Agent, or Firm* — Levine Bagade Han LLP

(57) ABSTRACT

Methods and devices described herein facilitate improved treatment of body organs and relates to surgical instruments, useful in endoscopic, laparoscopic and/or open surgical procedures to effectively remove a suspect region of tissue such as a polyp, abnormal growth, cyst, tumor, lesion, or other abnormality from a base tissue structure.

20 Claims, 23 Drawing Sheets

(56) References Cited

U.S. PATENT DOCUMENTS

| | | | | |
|---|---|---|---|---|
| 8,252,009 | B2* | 8/2012 | Weller | A61B 17/0218 227/175.1 |
| 8,328,061 | B2* | 12/2012 | Kasvikis | A61B 17/07207 227/175.1 |
| 2001/0045442 | A1 | 11/2001 | Whitman | |
| 2002/0198539 | A1 | 12/2002 | Sixto, Jr. et al. | |
| 2005/0263562 | A1* | 12/2005 | Shelton, IV | A61B 17/0686 227/176.1 |
| 2006/0151568 | A1* | 7/2006 | Weller | A61B 17/0218 227/175.1 |
| 2006/0241692 | A1* | 10/2006 | McGuckin, Jr. | A61B 17/07207 606/219 |
| 2007/0175955 | A1 | 8/2007 | Shelton et al. | |
| 2007/0213743 | A1* | 9/2007 | McGuckin, Jr. | A61B 17/00234 606/139 |
| 2008/0078807 | A1* | 4/2008 | Hess | A61B 17/0644 227/181.1 |
| 2009/0065552 | A1* | 3/2009 | Knodel | A61B 17/072 227/180.1 |
| 2010/0072251 | A1 | 3/2010 | Baxter, III et al. | |
| 2011/0068147 | A1* | 3/2011 | Racenet | A61B 17/072 227/180.1 |
| 2011/0089221 | A1* | 4/2011 | Masiakos | A61B 17/07207 227/180.1 |
| 2013/0068818 | A1* | 3/2013 | Kasvikis | A61B 17/07207 227/175.2 |
| 2013/0248578 | A1* | 9/2013 | Arteaga Gonzalez | A61B 17/07207 227/176.1 |
| 2014/0276968 | A1 | 9/2014 | Miksza et al. | |

* cited by examiner 148
140
154

140

148
172
176
174
178
140
176
176

TISSUE REMOVAL AND CLOSURE DEVICE

RELATED APPLICATIONS

This application is a non-provisional of U.S. Patent Application No. 62/196,785 filed Jul. 24, 2015. This application is also a continuation-in-part of U.S. application Ser. No. 13/028,148 filed Feb. 15, 2011. The entirety of both applications are incorporated by reference in its entirety.

FIELD OF THE INVENTIONS

The present invention relates to surgical instruments, useful in endoscopic, laparoscopic and/or open surgical procedures to effectively remove a suspect region of tissue such as a polyp, abnormal growth, cyst, tumor, lesion, or other abnormality from a base tissue structure.

BACKGROUND

Minimally invasive surgical procedures are becoming more common as surgeons use a variety of techniques to operate with reduced trauma to the body than with open surgeries. In general, minimally invasive surgical procedures are safer than open surgeries and allow the patient to recover faster and heal with less pain and scarring. Minimally invasive surgical procedures are typically performed with one or more incisions to the body where surgical instruments are inserted and maneuvered into the surgical site to treat the targeted tissue.

A polyp is an abnormal growth of tissue projecting from a base region of tissue, typically that includes a mucous membrane. Polyps can be attached to the surface of the mucous membrane by a narrow elongated stalk, in which case the polyp is said to be pedunculated. If the polyp is directly attached to the base region of tissue with no stalk, the polyp is said to be sessile. Polyps can be found in various regions within the body such as the colon, stomach, nose, urinary bladder, cervix, small intestines, and uterus.

Polypectomy performed via an endoscopic or laparoscopic procedure performed through the oral or anal cavities are much more preferred over open procedures. Polyps are conventionally removed using either electrical forceps or an electrosurgical wire loop that is positioned around the base of the stalk of the polyp where the device severs the polyp (or stalk) as well as coagulates the blood vessels in the stalk of the polyp. However, in any procedure using conventional devices, especially those performed minimally invasively, the physician must take care to remove the polyp or stalk while remaining safely spaced away from the base region of tissue. Otherwise, inadvertent removal of the base tissue can create additional trauma via an opening in the base tissue. For example, unintentionally creating an opening in an organ, including but not limited to, the colon, stomach, nasal cavity, urinary bladder, cervix, small intestines, or uterus can require immediate surgery to repair the opening. Moreover, repairing any opening created as a result of removal of suspect tissue can require complicated or time consuming stitching or suturing to close the opening in the base tissue of the organ. There is also a risk of post-surgical complications if the physician does not properly close the opening.

Many times polyps or other suspect regions of tissue are identified during examination procedure as opposed to a surgical procedure. The risks associated with inadvertently creating an opening in an organ during removal of suspect tissue can present a dilemma for a physician that first observes the polyp (or other suspect tissue) but is hesitant to remove it if the physician believes that it will be difficult to maintain a clean margin (i.e., a region of relatively healthy tissue) at the site of the excision. In such a case, the physician must refer the patient for a further surgical procedure to remove the suspect region of tissue for a biopsy.

FIGS. 1A and 1B assist in illustrating the issues presented above. For example, FIG. 1A illustrates an endoscopic view (e.g., a view of a cavity or organ using endoscopic visualization) of the base tissue 4 within an organ 2. As shown, because the initial examinations are often performed via a minimally invasive procedure, the limited area or tortuosity within the organ 2 increases the difficulty of navigating and manipulating tools to the site for removal of tissue and/or closing of openings within the tissue 4.

FIG. 1B illustrates two different polyps 6, where the polyp 6 on the upper portion of the figure connects to the base tissue 4 via a stalk 8. The polyp 6 on the lower portion of the figure directly extends from the base tissue 4 and contains a margin 10, which represents the transition of the polyp or suspect tissue 6 to the base tissue 4. In either case, a physician will only remove the polyp if the physician can be assured of removing the entire polyp without leaving suspect tissue behind. In addition, the physician will often be hesitant to remove such a region of tissue if there is a risk that the procedure creates an opening in the wall of an organ where such an opening could lead to further complications to the patient.

There remains a need for a device, methods, and systems to allow a physician to access difficult to reach anatomic regions and to remove a region of suspect tissue in its entirety, and to provide the physician with the ability to confidently secure the tissue that remains after the excision of suspect tissue.

SUMMARY OF THE INVENTION

Variations of the devices, methods and procedures described herein include combinations of features of the various embodiments or combination of the embodiments themselves wherever possible.

The present disclosure includes surgical devices for separating a region of tissue from a tissue structure and for use with a plurality of fasteners that can fasten the region of tissue adjacent to the separated tissue. The present disclosure also relates to devices and methods for the removal of internal tissue and, more particularly tissue removal and closure devices and methods of use. The devices and method described herein can be used to remove a suspect region of tissue, including but not limited to, a polyp, abnormal growth, cyst, tumor, lesion, or other abnormality that is found on a base region of tissue. The present disclosure describes the methods and procedures with respect to polyps but are not limited to such.

In one example, such a surgical device includes a shaft; a first jaw located at an end of the shaft, the first jaw having a first end and a second end and a working surface that extends along a length of the first jaw between the first end and the second end; a second jaw being coupled to the first jaw at the first end to allow the second jaw to move relative to the first jaw between an open position and a closed position; a boundary member operatively coupling the second jaw to the first jaw at the second end such that a distal end of the boundary member moves with the second jaw between the open and closed position while remaining engaged with the first jaw, wherein application of a tensile force on the boundary member retracts the boundary member to pull the second jaw towards the closed position; where the operatively coupling of boundary member to the first jaw and second jaw also forms a mechanical barrier at the second end that prevents the tissue structure from extending longitudinally beyond the working surface when the tissue structure is positioned transversely across the working surface between the first jaw and second jaw when the second jaw is in the closed position; a fastening track comprising a plurality of fastening openings located on the working surface to permit movement of the plurality of fasteners therethrough, the fastening track being adjacent to a first edge of the first jaw to permit movement of the fasteners therethrough; a cutting track adjacent to a second edge of the first jaw; and a cutting element moveable along the cutting track, where actuation of the cutting element along the cutting tract separates the region of tissue from the tissue structure secured by the second jaw in the closed position. In some variations, the first jaw is fixed at the end of the shaft such that the second jaw moves and the first jaw remains stationary when actuated.

In another variation, the surgical devices can include a shaft; a first jaw located at the end of the shaft, the first jaw having a first end and a second end and a plurality of openings that extends along a length of the first jaw between the first end and the second end; an actuating jaw being coupled to the first jaw at the first end and moveable between an open position and a closed position; a boundary member having a distal end coupled to the actuating jaw and being moveably engaged through the first jaw at the second end to form a barrier at the second end of the first jaw, where the boundary member remains engaged with the first jaw as the distal end of the boundary member moves with the actuating jaw when the actuating jaw moves between the open position and the closed position, such that application of a tensile force on the boundary member pulls the actuating jaw towards the closed position; wherein the barrier formed by the boundary member prevents the region of tissue from extending longitudinally beyond the plurality of openings in the first jaw while the actuating jaw is in the closed position when the tissue is positioned transversely to and between the first jaw and actuating jaw; where the plurality of openings comprises a cutting track extending adjacent to a plurality of fastening openings, the plurality of fastening openings configured to permit movement of the fasteners there through, where the plurality of fastening openings are adjacent to a first edge of the first jaw and where the cutting track extends adjacently to a second edge of the first jaw, where a length of the cutting track is greater than a length of the plurality of fastening openings; and a cutting element located within the cutting track and configured to cut the region of tissue secured between the first jaw and the actuating jaw when the first jaw and the actuating jaw are in the closed position.

Another variation of the device includes a shaft; a first jaw located at an end of the shaft, the first jaw having a first end and a second end and a working surface that extends along a length of the first jaw between the first end and the second end; a second jaw being coupled to the first jaw at the first end to allow the second jaw to move relative to the first jaw between an open position and a closed position; a fastening track comprising a plurality of fastening openings located on the working surface to permit movement of the plurality of fasteners there through, the fastening track being adjacent to a first edge of the first jaw to permit movement of the fasteners through; a cutting element moveable parallel to the fastening track, where actuation of the cutting element along the cutting tract separates the region of tissue from the tissue structure secured by the second jaw in the closed position; and where the cutting element further comprising a first extension slidably coupled to a portion of the first jaw and a second extension slidably coupled to a portion of the second jaw, such that as the cutting element moves along the first jaw, the first and second portion prevents the second jaw from moving away from the first jaw, where when the cutting element is in a distal position along the first jaw and in a proximal position along the first jaw, the second extension disengages from the second jaw to permit opening of the second jaw relative to the first jaw.

Yet another variation of the device includes a shaft; a first jaw located at an end of the shaft, the first jaw having a first end and a second end and a working surface that extends along a length of the first jaw between the first end and the second end; a second jaw being coupled to the first jaw at the first end to allow the second jaw to move relative to the first jaw between an open position and a closed position; a boundary member operatively coupled to the second jaw at a second end of the second jaw and is moveable when the second jaw is in the open position to form a mechanical barrier at the second end that prevents the tissue structure from extending beyond the working surface when the tissue structure is positioned transversely across the working surface between the first jaw and second jaw when the second jaw is in the closed position; a fastening track comprising a plurality of fastening openings located on the working surface to permit movement of the plurality of fasteners there through, the fastening track being adjacent to a first edge of the first jaw to permit movement of the fasteners through; a cutting track adjacent to a second edge of the first jaw; and a cutting element moveable along the cutting track, where actuation of the cutting element along the cutting tract separates the region of tissue from the tissue structure secured by the second jaw in the closed position.

Variations of the devices can also include a boundary member that is configured to advance away from the first jaw when the second jaw is in the open position such that the distal end of the boundary member remains coupled to the second jaw and a portion of the boundary member expands away from the first jaw to an extended profile, where the extended profile permits capturing of the tissue structure beyond the working surface when the second jaw is in the open position, and where proximal movement of the boundary member direct the tissue structure towards the working surface as the second jaw assumes the closed position.

The boundary member can be releasably coupled to the second jaw to permit detachment of the first and second jaw from the shaft, and further comprising a cartridge containing the plurality of fasteners.

The jaw assembly can be spring biased to the open position or the closed position.

In variations of the device, cutting track spans beyond the fastening track on the first and second end of the fixed jaw.

The cutting element disclosed herein can comprise a mechanical instrument such as a blade, an electrosurgical cutting apparatus, or a combination of both.

The devices described herein can have any number of parallel rows of fastening openings.

BRIEF DESCRIPTION OF DRAWINGS

FIG. 3B shows the operative assembly of FIG. 3A when positioned in a deployment configuration where the actuating jaw is nested against the fixed jaw with little or no space there between.

DETAILED DESCRIPTION

Methods and devices described herein provide for separating a suspect region of tissue from a base region of tissue and securing the base region of tissue that remains after the excision of the suspect tissue. Although the following description discusses the use of mechanical fasteners and a mechanical cutting instrument, any number of fastening modes and cutting modes can be employed in accordance with the disclosure herein as long as such modes do not conflict with the teachings disclosed herein. In addition, any number of combinations of aspects of various species, or combinations of the species themselves are within the scope of this disclosure. In addition, the methods, devices and systems described herein are well suited towards endoscopic procedures, but are not limited to such procedures. The disclosure can be combined with open procedures as well.

Figure 2:
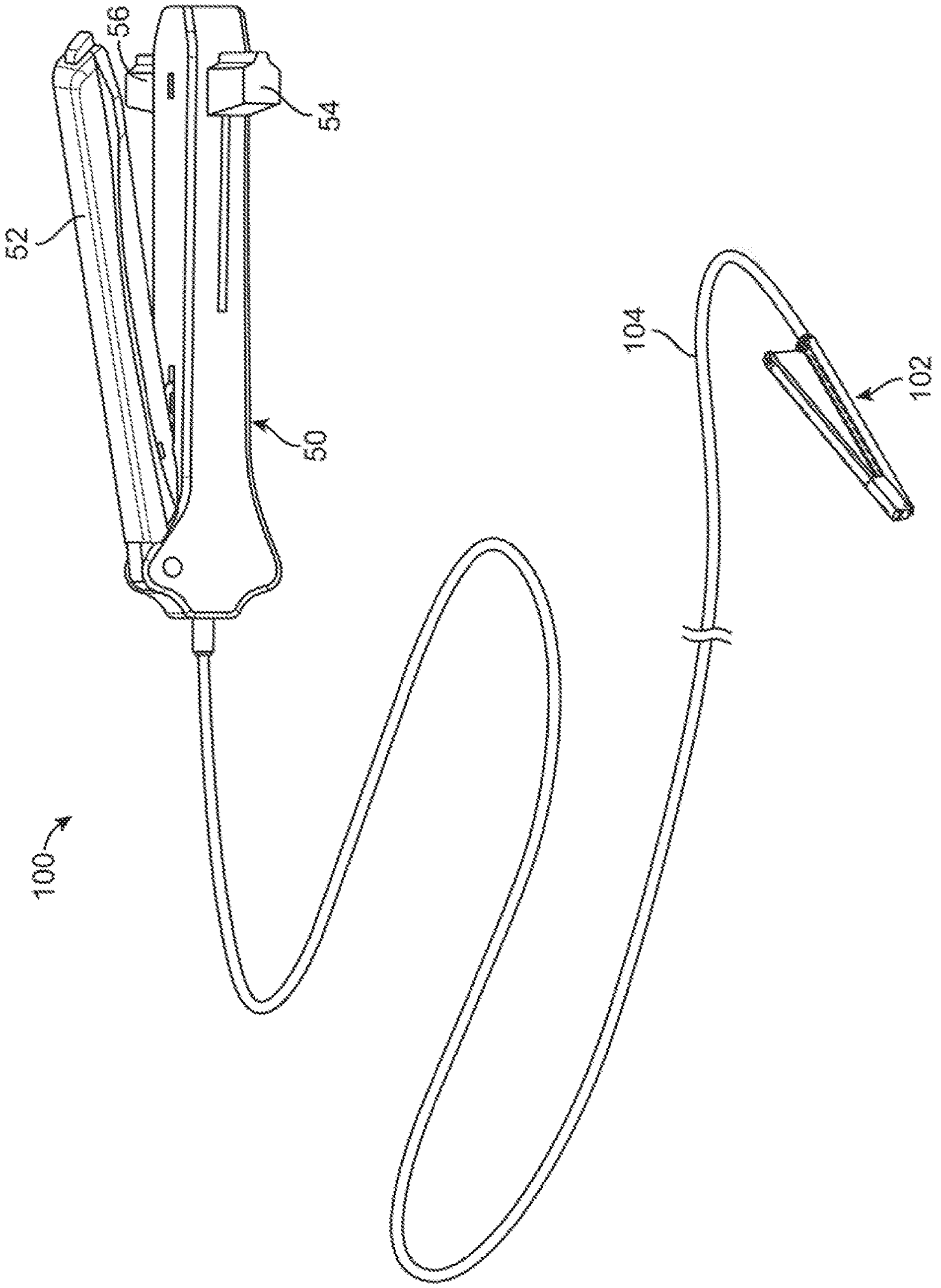
FIG. 2 illustrates an example of a surgical device including an operative assembly that can secure, sever and fasten a region of tissue.

FIG. 2 illustrates an example of a surgical device 100 according to the present disclosure where the device 100 includes an operative assembly 102 that can secure, sever and fasten a region of tissue as described below. The sequence of operation of severing, securing, and fastening the region of tissue can occur in any order as desired by the user or depending upon the application. In addition, the device 100 can perform any combination of severing, securing, and fastening tissue as opposed to all of the operations.

In the variation illustrated by FIG. 2, the device 100 includes a flexible shaft 104 coupled to the operative assembly 102. Additional variations of the shaft 104 can include a rigid, malleable, and/or steerable shaft. Furthermore, the shaft 104 can be driven via any robotic manipulator or system as required. In additional variations, the operative assembly 102 can be coupled to a distal end of an endoscope, which functions as a shaft, and where any linkages or control wires extend through the endoscope to a control assembly at the user end.

In the illustrated variation, the device 100 includes a control assembly 50 comprising a handle with various actuators, including but not limited to a clamping lever 52, cutting actuator 54 and fastening actuator 56. Variations of the device 100 include a control assembly 50 having an actuator that controls one or more actions of the operative assembly 102. For example, a single lever can be configured to clamp the suspect tissue, while a second lever can be actuated to cut and fasten the respective tissue sections. In addition, as discussed below, variations of the device 100 can include a steerable operative assembly 102 or a steerable shaft 104 where the steering controls can be located on or adjacent to the handle 50.

Figure 3A:
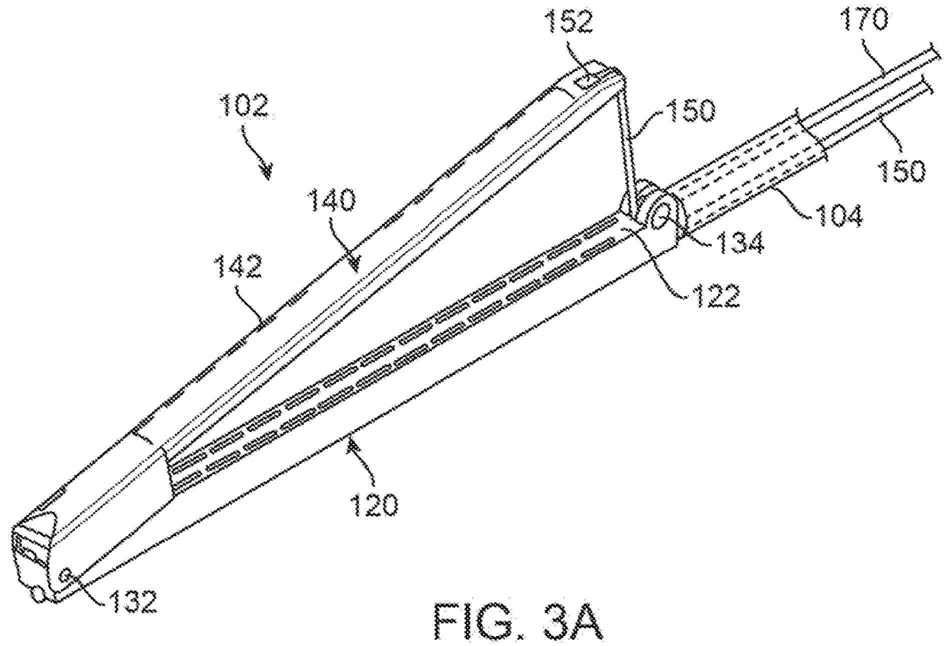
FIG. 3A illustrates a magnified view of the operative jaw assembly of FIG. 2 where the operative assembly is in an open configuration.

FIG. 3A illustrates a magnified view of the operative jaw assembly 102 of FIG. 2 where the operative assembly 102 is in an open configuration. In this example the assembly comprises a fixed jaw 120 coupled to a shaft 104 and where a first end of the fixed jaw 120 couples to an actuating jaw 140 via a pivot member 132. However, any number of configurations that allow for relative movement between the jaws are within the scope of this disclosure. For example, such coupling structures can include alternate variations, such as intrinsic joints, living hinges, etc. that allow a pair of jaws to operatively secure tissue against a working surface 122. In addition, an alternate operative jaw assembly can include a configuration where both ends of the jaw assembly move in a normal or orthogonal direction relative to a working surface 122 of one of the jaws.

As discussed below, the working surface 122 can include features necessary to perform the medical procedure. Accordingly, any portion of the operative assembly 102 can include markings 142 or visual indicators (e.g., illumination, electrodes, sensors, etc.) to assist the physician in performing the procedure. For example, marking 142 allows the physician to determine which part of tissue captured by the jaws would be adjacent to a cutting line of the device.

Figure 1A:
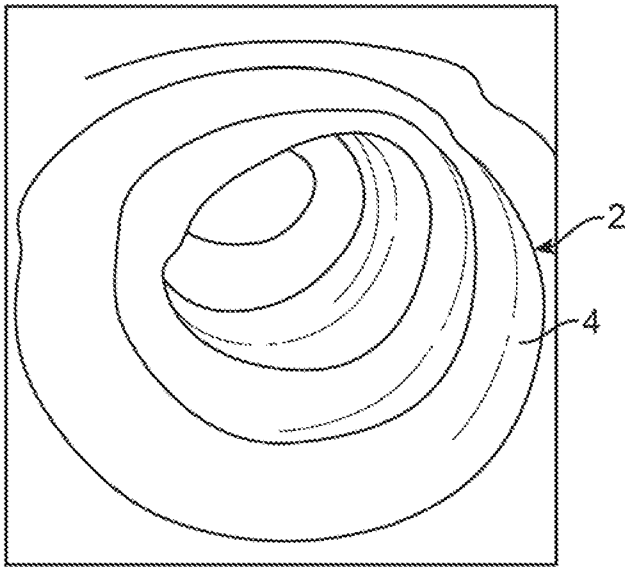
FIG. 1A illustrates a view of a cavity or organ using endoscopic visualization of a base tissue within an organ.
Figure 1B:
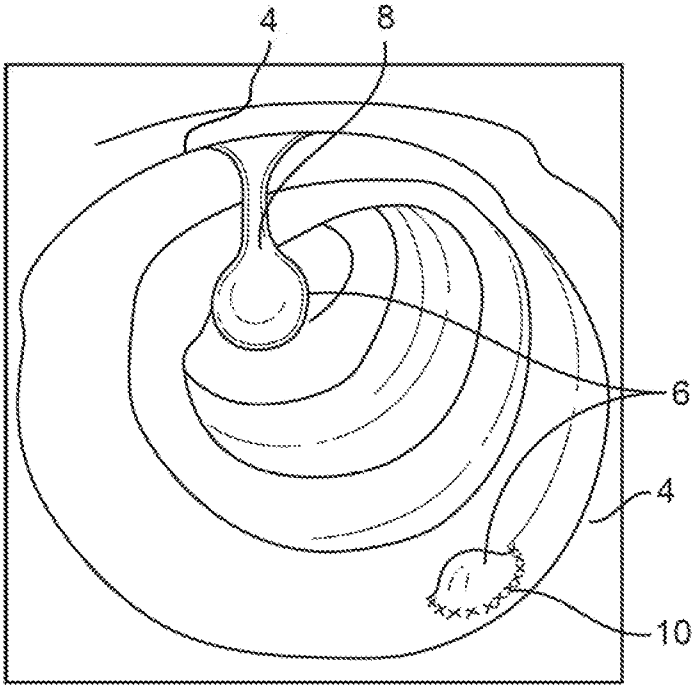
FIG. 1B illustrates two different regions of suspect tissue.
Figure 3B:
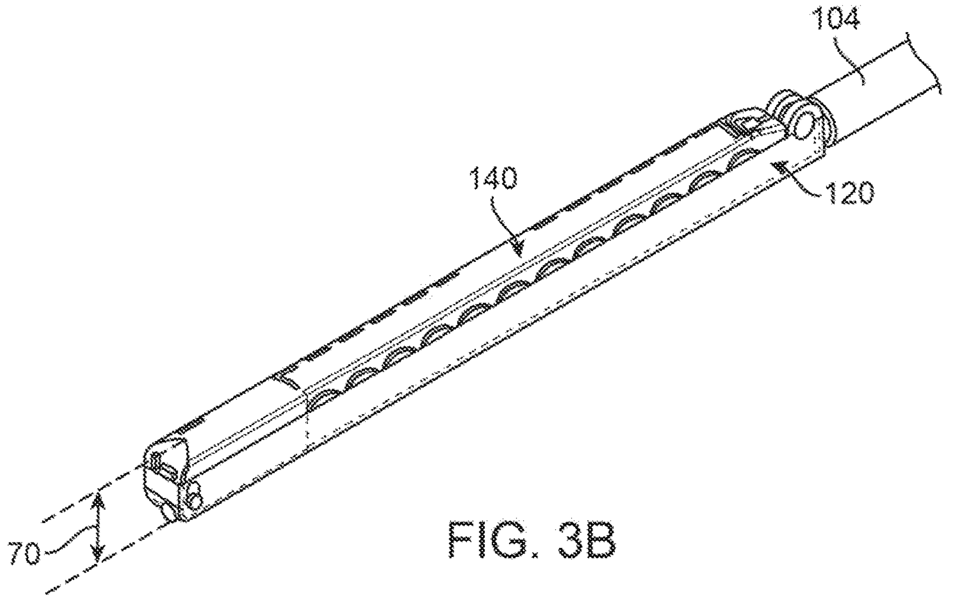

As noted above, the fixed jaw 120 and actuating jaw 140 function to operatively secure tissue or other structures there-between. In the variation shown, the "non-pivoting end" of the jaw assembly (i.e., the end opposite to the pivoting end) is joined with a link member 150. The illustrated link member 150 comprises a cable, however, alternative structures can be used as a link member, including but not limited to, ribbon, filament, suture material, deformable cannula, films, or similar structure that functions as described herein. This boundary member 150 is configured to draw the jaws towards a closed configuration (as discussed below) or to a delivery configuration as shown in FIG. 3B. The boundary member 150 can include a distal end 152 that is coupled to an end of the actuating jaw 140 where a medial portion of the boundary member 150 extends through a portion of the fixed jaw and ultimately through the shaft 104. As shown, the boundary member 150 can rely on one or more bearings or pins 134 to allow for bending of the boundary member 150. As seen in FIG. 1, the pivoting end of the jaw assembly may be at the distal end of the operative assembly 102, and the non-pivoting end of the jaw assembly may be at the proximal end of the operative assembly 102. Alternately, the pivoting end of the jaw assembly may be at the proximal end of the operative assembly 102, and the non-pivoting end of the jaw assembly may be at the distal end of the operative assembly 102. FIG. 3A also shows that the operative assembly 102 can include any additional members 170 that extend through or adjacent to the shaft 104, where the member 170 is used to actuate other features of the device (e.g., fasteners, cutting element, etc.) as described below.

In certain variations, the distal end 152 of the boundary member 150 can be detachably coupled to the actuating jaw 140 and/or the fixed jaw 120. The boundary member 150 also provides a barrier/mechanical block/mechanical stop to prevent tissue from extending longitudinally beyond a working surface 122 of the fixed jaw 120 or a working surface (not shown) of the actuating jaw 140.

The variation illustrated in FIG. 3A also provides an added advantage in that a tensile force or pulling force applied on the boundary member 150 or any structure coupling the boundary member 150 to the handle achieves closure of the jaw assembly. Likewise, when clamped and the boundary member is in a state of tension, the cutting element can be driven by another tensile force or pulling force applied on the linkage 170 that drives the cutting element. This configuration prevents opposite forces (e.g., a compressive and a tensile) being applied on linkages or structures in the device to clamp and then cut tissue. In use, the physician is able to apply a "pull-pull" operation to clamp and then cut the tissue.

FIG. 3B shows the operative assembly 102 of FIG. 3A when positioned in a deployment configuration where the actuating jaw 140 nests against the fixed jaw 120 with little or no space there between (in certain variations, the jaws can have a slight separation or spacing). Such a configuration minimizes a dimensional profile (e.g., a diameter, cross sectional area, height, width, etc.) of the access device or insertion point used to deliver the device 100 to the target area. As shown, the jaw height 70 is minimized in the delivery configuration. By minimizing the jaw height 70, the operative assembly 102 is able to be introduced more easily to an operative site through a natural orifice of the patient or through an incision in the body of the patient.

Figure 4A:
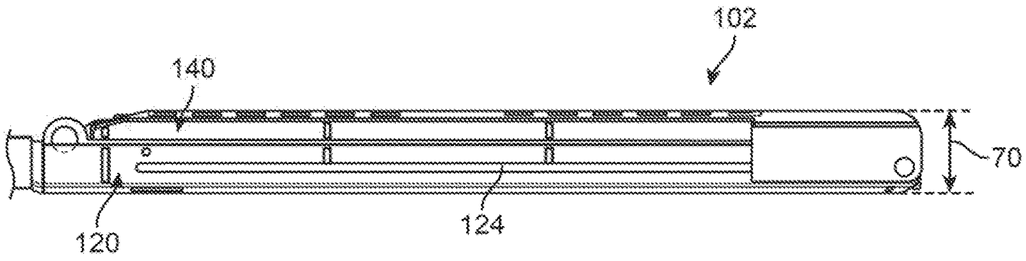
FIGS. 4A to 4C shows side views of the operative jaw assembly, showing a side or edge of the fixed jaw that is adjacent to a cutting track (not shown).
Figure 4B:
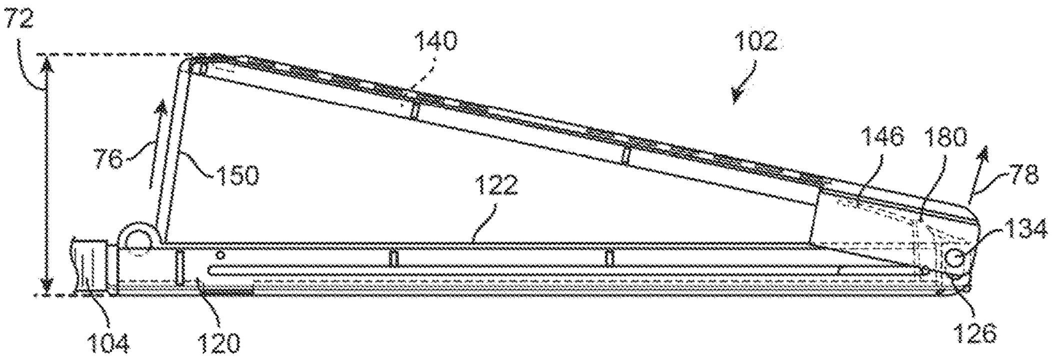
Figure 4C:
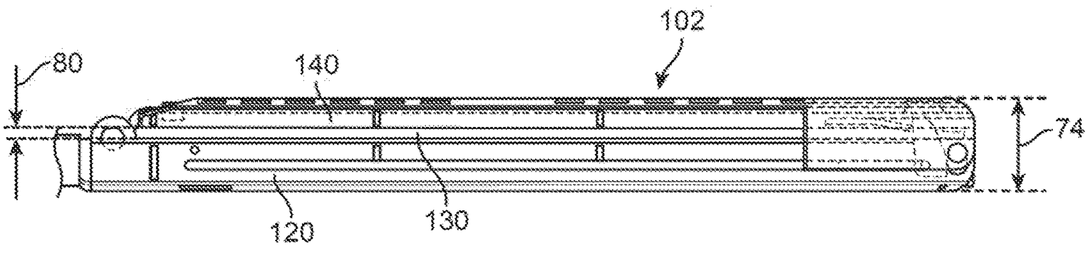

FIGS. 4A to 4C shows side views of the operative jaw assembly 102, showing a side or edge of the fixed jaw 120 that is adjacent to a cutting track (not shown). This variation of the assembly 102 includes a window 124 in which a physician or operator can view the location of a cutting element 180 as shown in FIG. 4B. As noted above, the operative jaw assembly 102 of FIG. 4A is in a delivery configuration where the fixed jaw 140 contacts (or has a slight gap 130) from the fixed jaw 120.

FIG. 4B illustrates an open configuration of the operative assembly 102. The actuating jaw 140 shown is illustrated in a hidden or transparent view for purposes of illustrating additional features of the assembly 102. As shown, the profile of the assembly (notably the end portion adjacent to the shaft 104) increases to an open jaw height 72 as the actuating jaw 140 and boundary member 150 move in direction 76. FIG. 4B shows a spring member 146 that can be used to bias the actuating jaw 140 towards the open configuration, such that movement of the boundary member 150 allows the jaw to assume the open configuration.

FIG. 4B also shows an optional configuration where the fixed jaw 120 includes a slot 126 opening in that allows a pivot member 134 to move in a direction that is normal to the working surface of the jaw 122. Such a feature allows an end of the actuating jaw 140 to pivot and move in the axial direction as noted by arrow 78 (i.e., allowing for two degrees of freedom: rotational and axial movement of the end of the jaw). The axial and rotational movement permits the operative jaw assembly 102 to assume a closed position, as shown in FIG. 4C, where the closed position allows for a space 80 between the actuating jaw 140 and the fixed jaw 120 where the space 80 accommodates tissue clamped therebetween. Additional variations of the device include configurations where the closed configuration is similar or the same to the delivery configuration where there is no space between the jaws. Alternatively, a variation of the device includes a configuration where the delivery configuration has a space between the clamping jaws.

Figure 4D:
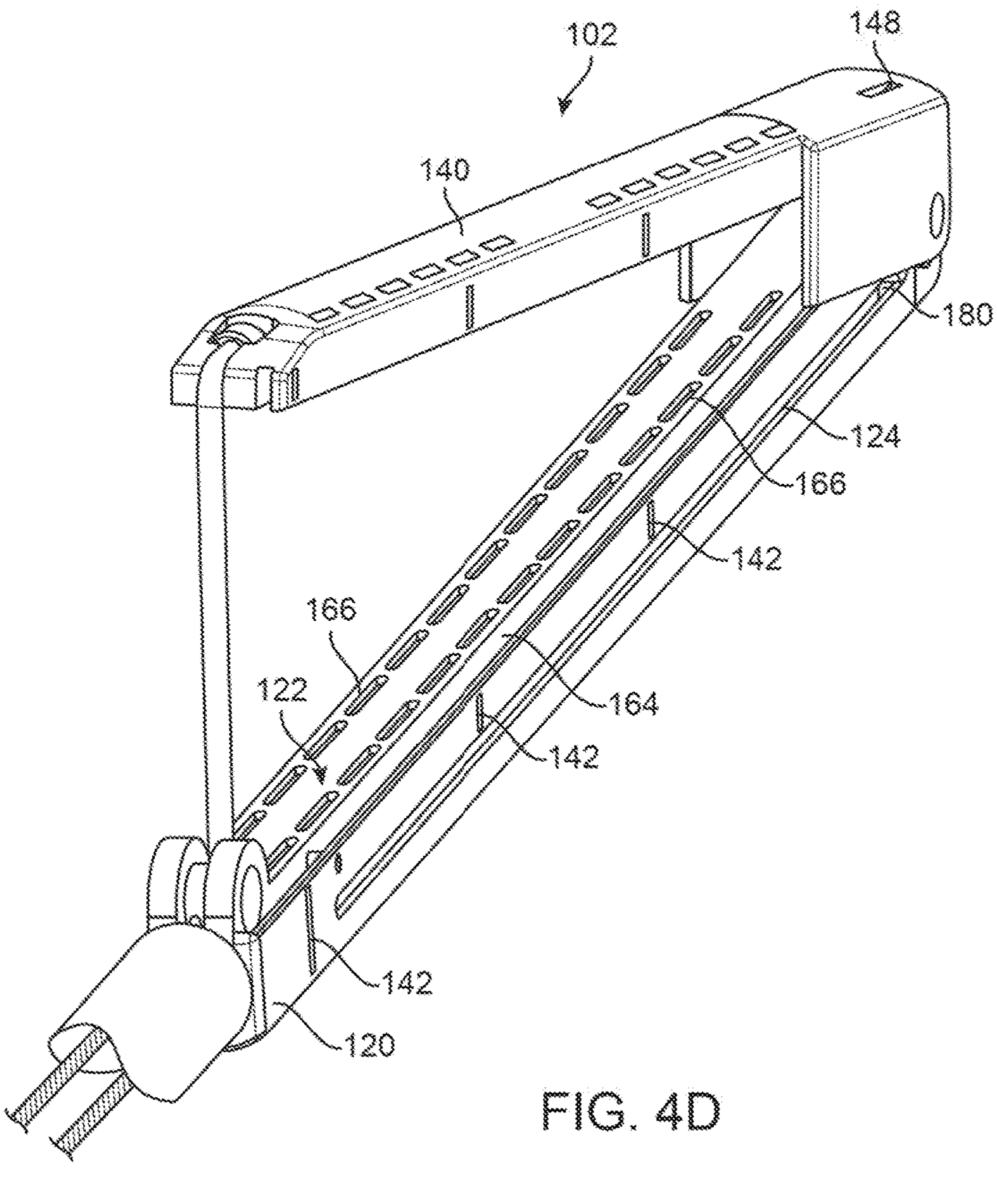
FIG. 4D is a perspective view of an operative jaw assembly to illustrate the working surface of the fixed jaw.

FIG. 4D is a perspective view of an operative jaw assembly 102 to better illustrate the working surface 122 of the fixed jaw. As illustrated, the working surface 122 can include a plurality of openings necessary for the jaw assembly 102 to perform various functions. For example, in the illustrated variation, the working surface comprises a fastening track comprising two rows of openings 166. These openings allow tissue fasteners to exit the fixed jaw 120 and secure tissue (as discussed further below). In certain variations, the fasteners comprise staples. However, the device can employ any number of tissue fixation modes (e.g., tissue fasteners, clips, adhesive, sutures, energy The working surface 122 of FIG. 4D also includes a cutting track 164 that allows a cutting element 180 to cut through the tissue or structure secured by the clamp. In the illustrated variation, the cutting track 164 spans beyond the fastening track (i.e., is longer than the fastening track when measured longitudinally along the working surface 122). In alternate variations, the fastening track can span beyond the cutting track 164. As discussed below, this ensures that the cutting element 180 severs or cuts through an entire length of the tissue/structure secured within the operative jaw assembly 102, which avoids creating a partial cut that prevents removal of the secured tissue from the site. The actuating jaw 140 is also shown to have a nesting opening 148 that can secure a cutting element 180 from moving when the jaw assembly is in the delivery configuration and/or in the open configuration. For example, when the assembly 102 is in the delivery configuration, the actuating jaw 140 moves toward the fixed jaw 120 such that a portion of the cutting element 180 is positioned within the opening 148. This prevents inadvertent actuation of the cutting element 180.

Variations of the device 100 can include any number of markings 142 located on an exterior of the device. In the illustrated variation, the markings 142 along the window allow a physician to observe the progress of the cutting element 180 as it moves through the cutting track 164. In addition, the examples above show the fixed jaw as containing the cutting element and houses the fasteners. However, variations of the device and methods can include a configuration where either jaw can be the fixed/working jaw and that either the fixed or movable jaw can include the fasteners and/or cutting element.

Figures 5A, 5B, 5C:
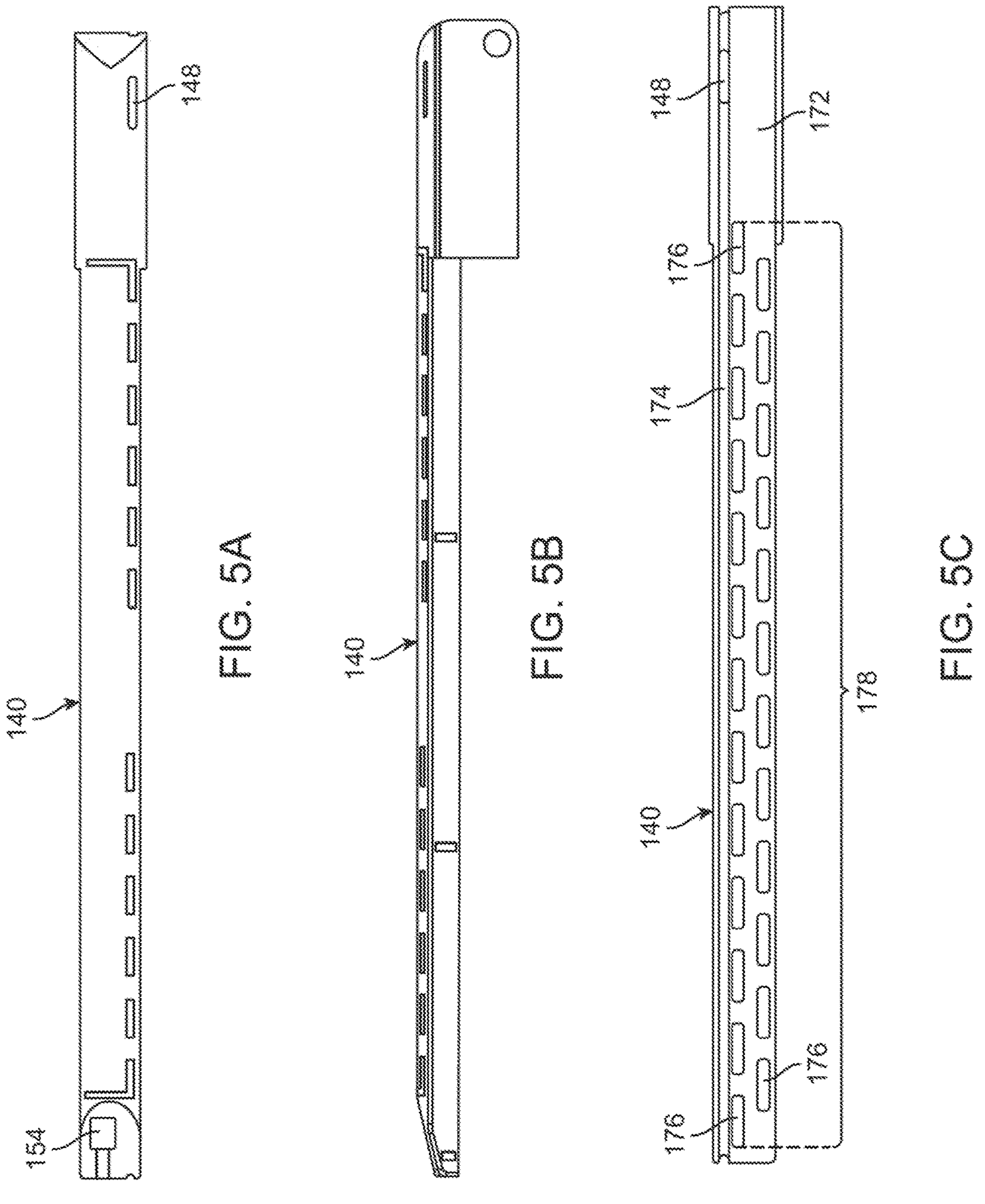
FIGS. 5A to 5C show respective top, side, and bottom views of an actuating jaw.

FIGS. 5A to 5C show top, side, and bottom respective views of an actuating jaw 140. In some variations of the assembly, a boundary member can be removably coupled to an actuating member 140. For example, as shown, FIG. 5A illustrates the actuating jaw 140 including a retaining groove 154 that allows for connection of the boundary member.

Removal of the boundary member may be necessary for disassembly of the jaw assembly when loading fasteners, cleaning the device, replacing the cutting element, etc. Any number of temporary fastening structures can be used to couple the boundary member to the jaw assembly. In additional variations, the boundary member can be fixedly attached to the jaw member. FIG. 5C illustrates a working surface of the actuating jaw 140 including a cutting track 174 adjacent to an edge of the actuating jaw 140. The cutting track 174 of the actuating jaw 140 will align with the cutting track of the fixed jaw 120 when in the delivery and/or closed position. As shown, the actuating jaw 140 can also include a fastening track 178 that contains a plurality of cavities 176. In the example shown, the cavities 176 form two rows but any number of rows is within the scope of the disclosure. The cavities 176 can be shaped to assist in directing of the fasteners upon deployment of the fasteners in tissue. As shown, the fastening track is adjacent to an opposite edge of the fixed jaw 140 and is shorter in length than the cutting track 174 when measured along the working surface.

Figures 6A, 6B, 6C:
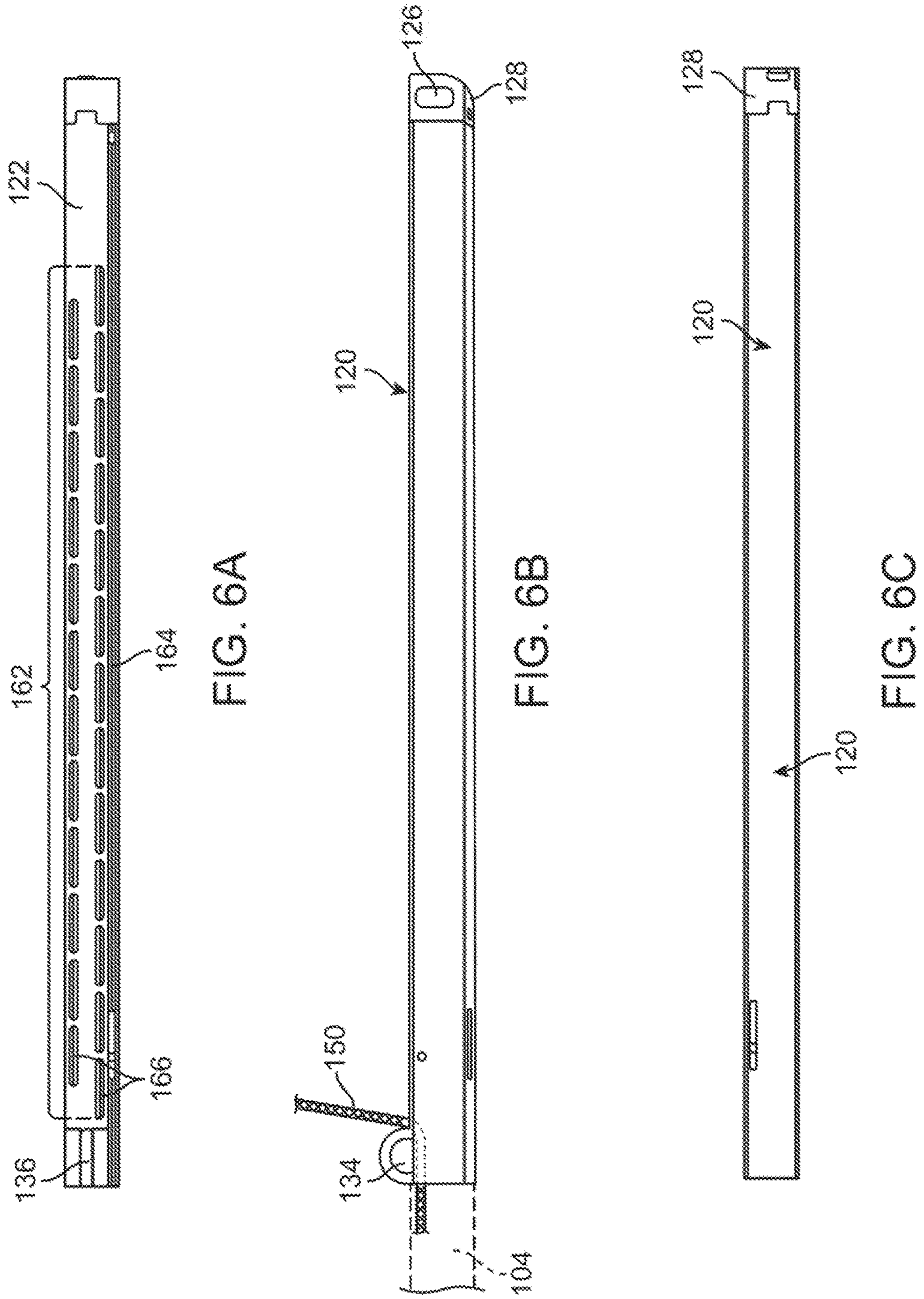
FIGS. 6A to 6C show respective top, side, and bottom respective views of a fixed jaw.

FIGS. 6A to 6C show top, side, and bottom respective views of a fixed jaw 120. As with the variation shown in FIGS. 5A to 5C, the working surface 122 of the fixed jaw includes a plurality of openings that respectively mate with the openings on the working surface of the actuating jaw 140. In the illustrated variation, the fastening track 162 comprises two rows of openings 166 that allow for fasteners to deploy through the working surface 122 into tissue captured within the jaw assembly. Again, any number of rows or openings can be used with the designs shown herein. In addition, for the illustrated variation, the cutting track 164 spans beyond a length of the fastening track 162. For example, when the fastening track 162 comprises a plurality of openings containing fasteners, the length of the cutting track will span beyond the length of the jaw that contains the openings. However, alternate variations of the device can include one or more cutting tracks that extend equal to or less than the span of the fastening track. As with the actuating jaw described above, the fastening track 162 is adjacent to an edge of the fixed jaw 120 while the cutting track is adjacent to an opposite edge of the jaw 120.

FIG. 6B also illustrates a boundary member 150 being operatively coupled to the the fixed jaw 120. In this example, the boundary member 150 is coupled through a slot or opening 136 in the fixed jaw that resides under a pivot or bearing 134 that is coupled to the fixed jaw 120. In alternate variations, the slot or opening 136 can extend through a body of the fixed jaw. In any case, the boundary member 150 can be coupled to the fixed jaw so that the boundary member 150 operatively couples the actuating jaw to the fixed jaw at an end of the assembly such that a distal end of the boundary member moves with the actuating jaw through the open and closed positions while remaining engaged to the fixed jaw. In the variations shown above, the boundary member is coupled to an end of the jaw that is adjacent to a shaft 104. However, additional variations of the device can include a boundary member that tends through a length of the jaw assembly so that it operatively couples the ends of the jaw assembly farthest from the shaft. In such a case, the mouth of jaw assembly opens in a distal oriented manner as opposed to the proximal oriented manner shown in FIG. 2 and above.

FIG. 6C illustrates a bottom view of the fixed jaw assembly 120. As shown, the jaw assembly 120 can comprise one or more components. In the illustrated example, the jaw assembly 120 includes a main body and an extension member 128 that houses the slot 126 that permits coupling of the actuating jaw to the fixed jaw 120. Clearly, it is within those skilled in the art to construct a jaw assembly from any number of components.

Figure 7A:
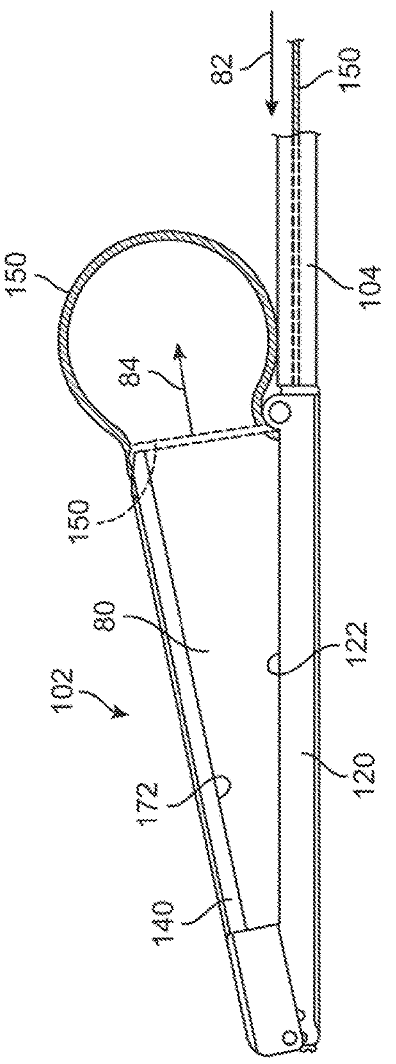
FIGS. 7A to 7C illustrate additional variations of a jaw assembly where a boundary member can be configured to advance away from the fixed and/or actuating jaws to increase an area of an operative space of the device.
Figure 7B:
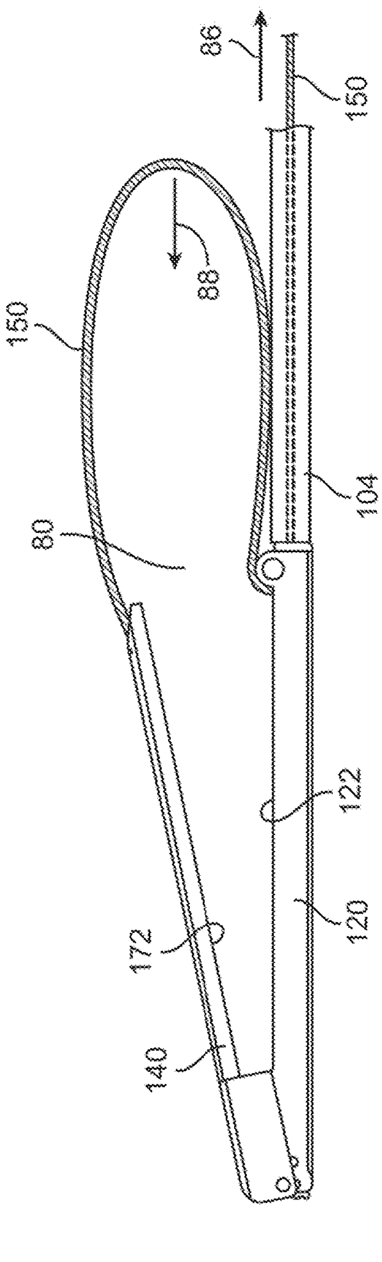
Figure 7C:
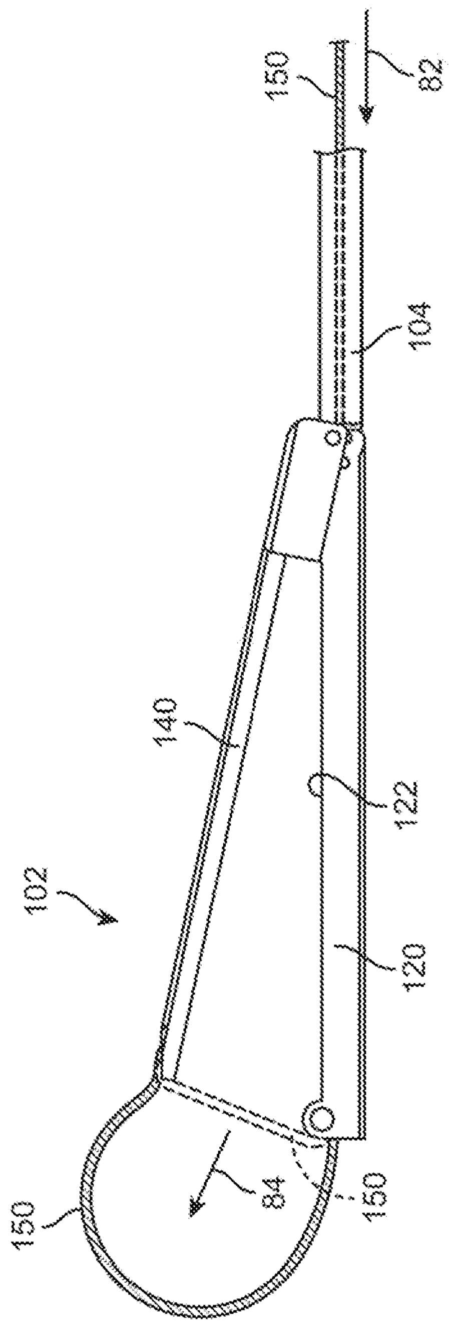

FIGS. 7A to 7C illustrate additional variations of a jaw assembly 102 where a boundary member 150 can be configured to advance away from the fixed 120 and/or actuating 140 jaws. For example, as shown in FIG. 7A, the operative jaw assembly 102 can assume a primary open configuration via, for example, spring biasing of the actuating jaw 140 relative to the fixed jaw 120 (as illustrated above). This configuration creates an operative space 80 defined by the area between the boundary member 150 (as shown by hidden lines) and jaw members 120 and 140. The primary open configuration yields an operative space that does not extend in an axial direction beyond the working surfaces 122, 172 of the jaws 120 and 140 while still allowing tissue to be pulled across and beyond the working surface in a transverse direction (see FIGS. 8A to 8F below). However, in certain variations, a physician can actuate the device to an extended open configuration (such as shown in FIG. 7B), for example, by applying a force 82 that moves the boundary member 150 at an operative end of the device. The actuation force 82 produces movement 84 of the boundary member 150 from a primary profile (for example as denoted by the boundary member 150 configured in a straight line between jaws as shown in FIG. 7A), to an extended open configuration (such as shown in FIG. 7B) where the boundary member advances away from the jaws in direction 84. This extended open configuration increases the operative space 80 area between the jaws and boundary member but the operative space 80 now extends beyond the working surfaces 122 and 172 of the jaw members 120 and 140. In order to achieve the extended open configuration the boundary member 150 should have sufficient column strength such that can it does not buckle within the shaft 104 when the actuation force 82 applies a compressive force. Alternatively, or in combination, the portion of the boundary member 150 within the shaft 104 can be sized in close tolerance with a tube or passage to prevent buckling of the boundary member 150 within the shaft 104.

This increase in operative space provides more room for a physician to maneuver larger regions of tissue into the operative space (e.g., for handling large tumors or tissue), to increase angular access to tissue, to accommodate two or more devices to grab tissue, etc. The extended open configuration can be limited to a semicircle (such as shown in FIG. 7A) or can be further extended (such as shown in FIG. 7B). Moreover, the boundary member 150 can include intrinsic joints, flex joints, varying degrees of thickness, etc., to provide a preferential shape when in the extended open configuration. Moreover, the boundary member can be shape set, and/or comprise a shape memory alloy to form any particular desired shape. Furthermore, while FIGS. 7A to 7C illustrate the boundary member 150 as extending through a length of the shaft 104, in some variations the boundary member need not extend through the shaft. In some variations of the device can include a wire or other coupling member that is intermediate to the boundary member 150 and device controls at the operator end of the device.

FIG. 7B illustrates an elongated extended opening as a retraction force is applied to retract the boundary member 150 from the extended open configuration towards the primary open configuration. The boundary member 150 can be actuated by the operator through any number of configurations on the handle. The movement of the boundary member 150 draws or urges tissue located within the extended operative space 80 towards the working surfaces 122 172 of the jaws 120 140. In some cases, a physician will retain tissue in the operative space 80 with the aid of a grasping device such as a forceps, clamp, suture, etc. Once the physician positions the boundary member 150 in the primary open configuration (see e.g., FIGS. 4B and 4D) the boundary member 150 and jaws 120 140 prevent any tissue located in the operative space 80 from extending beyond the working surfaces 122 172 of the jaws. The jaws 120 140 then assume the closed configuration (e.g., FIG. 4C) where a physician can continue the procedure. The ability to prevent tissue from extending longitudinally beyond the working surfaces of the jaws and to remain within the operative space 80 (see FIG. 7B) ensures that the entire length of the tissue held by the jaw members will be cut and/or fastened. Such a feature may be significant when attempting to remove a region of suspect tissue from a wall of an organ or other tissue structure. In some variations, the boundary member need not be retracted to the primary open configuration. In some variations, the boundary member may remain in a partially extended open configuration.

FIG. 7C illustrates another variation of an operative assembly 102 as described above, but in this example, the boundary member 150 of the operative assembly 102 is positioned on an end of the jaw members 120 140 that is opposite to a shaft 104 of the device.

FIGS. 8A to 8F illustrate an example of the devices described above when used to remove a region of suspect tissue that is attached to a base tissue or a wall of a tissue structure. As noted above, a region of suspect tissue or polyp 6 directly extends from a base region of tissue 4 (including but not limited to a wall of an organ). The suspect tissue 6 often contains a margin 10 that extends into the base tissue 4. In some cases, the margin 10 is difficult to identify with certainty so a physician attempting to remove the suspect tissue 6 will want to remove a section of the base tissue 4 to ensure that the margins of the suspect tissue are excised.

Figure 8A:
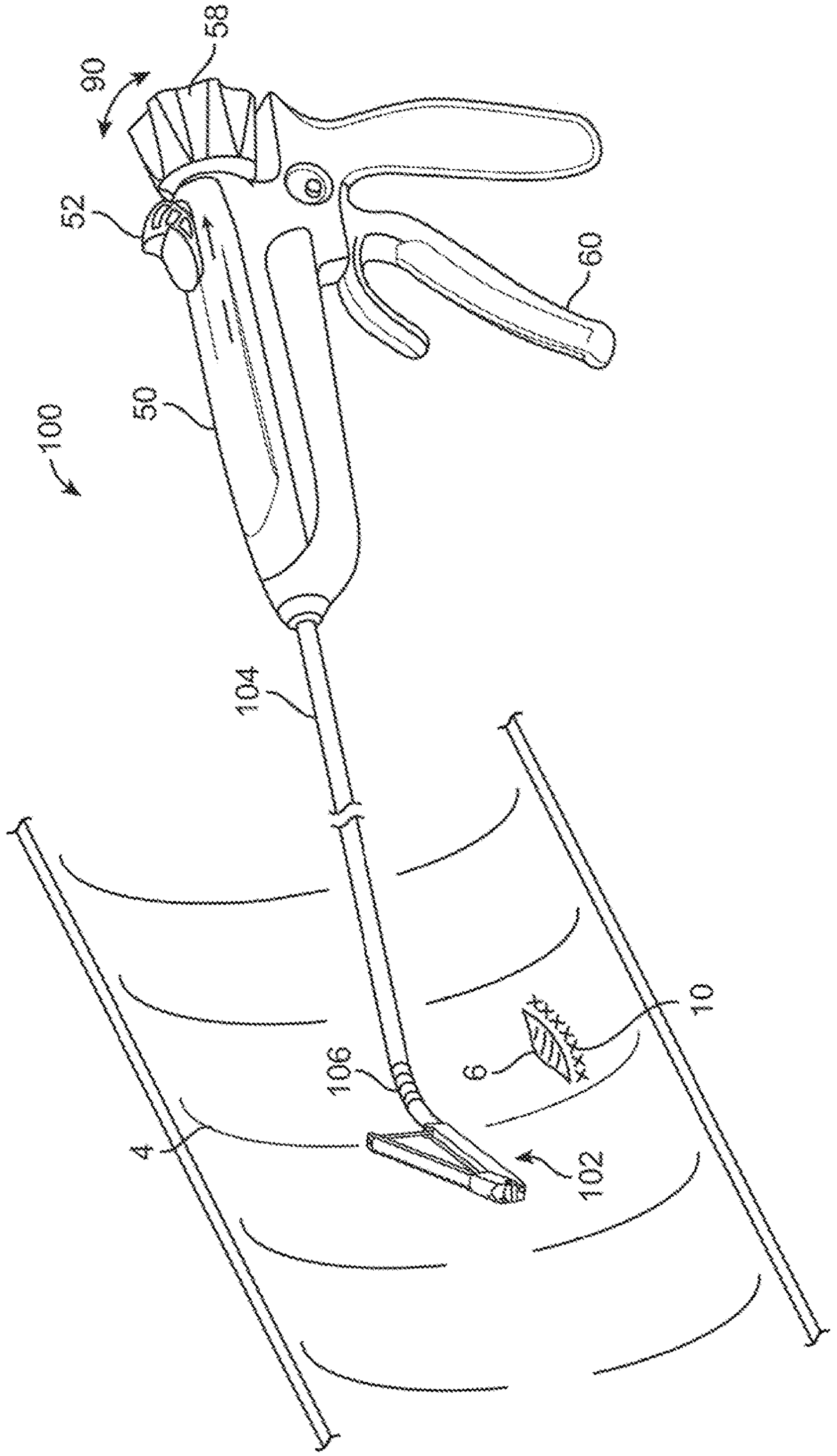
FIGS. 8A to 8F illustrate an example of the devices described above when used to remove a region of suspect tissue that is attached to a base tissue or a wall of a tissue structure.

FIG. 8A illustrates an example of a device 100 as described herein, where a physician advances an operative assembly 102 of the device 100 adjacent to a region of suspect tissue 6 located on a base region 4 or wall of an organ. In most variations, the device 100 will include controls, including but not limited to rotational/steering controls 58 where rotation 90 corresponds to rotation of an articulating section 106 of the shaft 104 that allow for rotation/steering of the operative assembly 102. The device can also include clamping controls 52 as well as fastening and cutting controls 60. In the illustrated variation, the cutting and fastening operations can be driven by a single control 60. However, variations of the device allow for separate controls, such as shown above in FIG. 2.

The operative assembly 102 is also illustrated as being directly coupled to a shaft 104 of the device 100 for illustrative purposes only. In some variations, the operative assembly 102 and other features of the device 100 can be advanced through or incorporated with an endoscope type device.

Figure 8B:
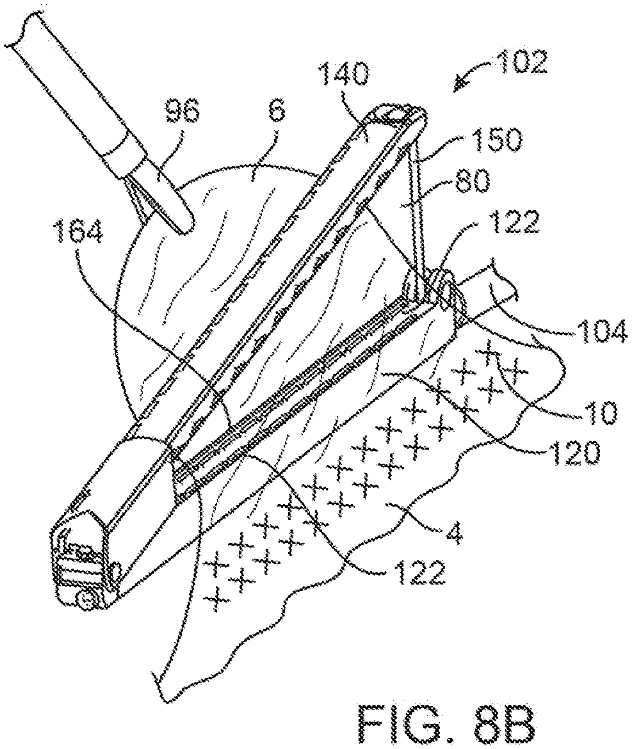

FIG. 8A illustrates a condition where the operative assembly 102 is positioned adjacent to the suspect region of tissue 6 so that a grasping device 96 can draw the suspect tissue 6 transversely across the working surface of the device, as shown in FIG. 8B. As noted above, the operative space 80 of the operative assembly 102 is bounded by the jaw members 120 140 as well as the boundary member 150. As a result, the tissue must be drawn transversely to the operative space and/or working surface (as discussed in FIGS. 7A and 7B). In some variations where the boundary member assumes an extended open configuration, the tissue must still be drawn transversely to the jaws since the boundary member will create a closed boundary of the operative space. As shown, the suspect tissue 6 is drawn from an edge of the assembly 102 that contains the cutting track 164 across the working surface 122 and beyond the edge of the assembly 102 adjacent to the fastening track 162. In some variations, the suspect tissue may be first drawn across the edge of the assembly 102 adjacent fastening track 162.

Figure 8C:
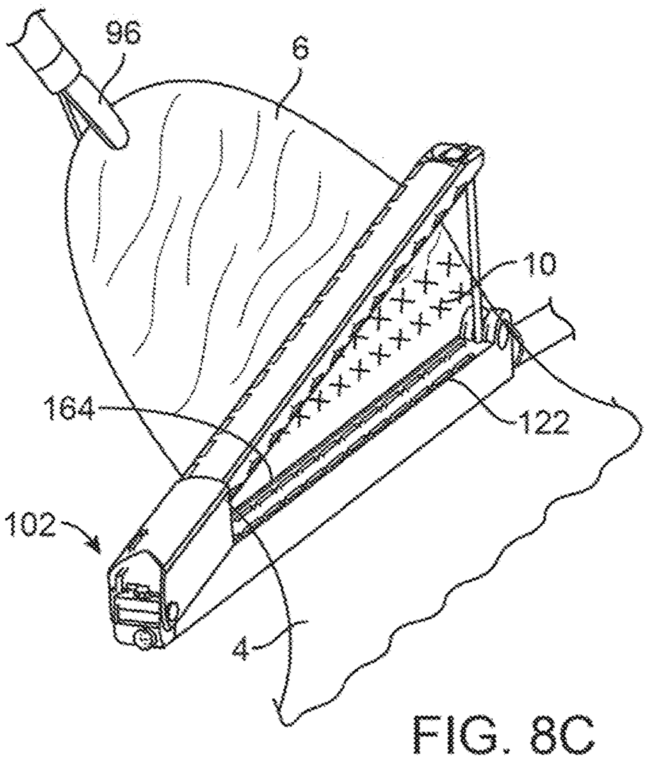

FIG. 8C illustrates continued movement of the suspect region of tissue 6 until the margin 10 of the suspect tissue 6 is also drawn across the working surface 122 of the assembly 102. The physician will continue to move the tissue until a region of base tissue 4 is adjacent to the working surface 122 of the assembly 102. Positioning the fastening track closer to the margin 10 than the cutting track assists with removing an entirety of the suspect tissue 6 while securing the adjacent base region 4.

Figure 8D:
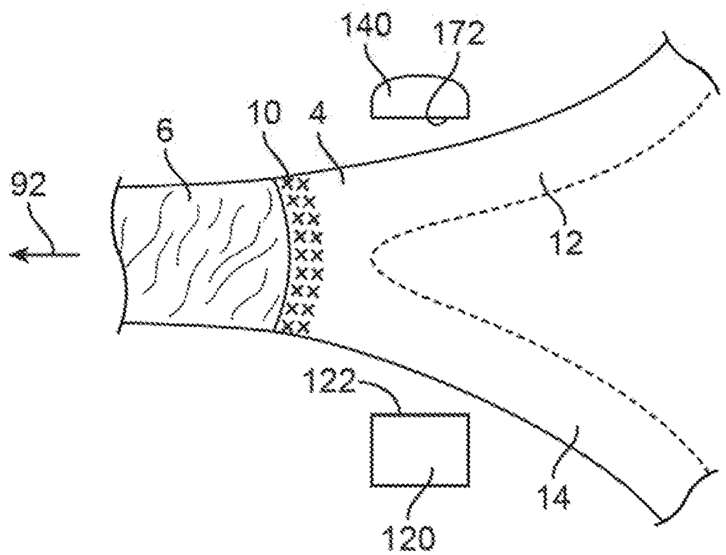
Figure 8E:
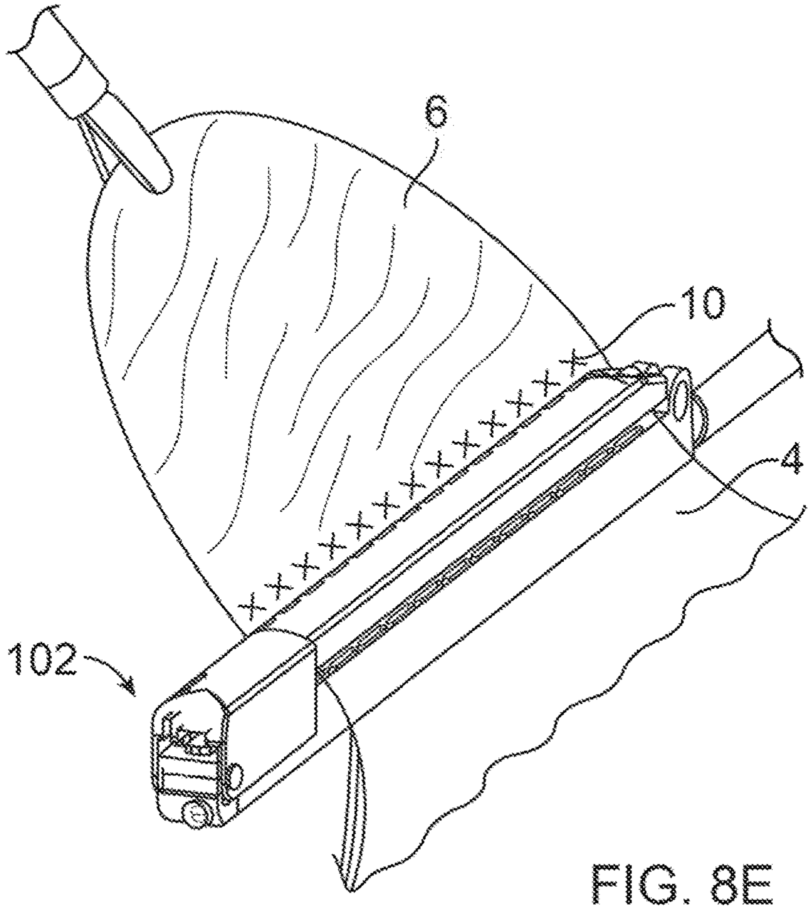

FIG. 8D illustrates a schematic side view of the suspect region of tissue 6, margin 10 and tissue wall 4 being transversely moved across the jaw members 120 140. As shown, pulling the wall of the tissue 4 into the operative space of the jaw causes a first region 12 and a second region 14 of the wall 4 that is adjacent to the suspect tissue 6 to become located adjacent to the working surfaces 122 172 of the jaw members 120 140. Actuation of the jaw members 120 140 to the closed position, as shown in FIG. 8E, causes the first region 12 and second region 14 of the wall 4 to contact and become a clamped or joined region of tissue 16 (as seen in FIG. 8E). In some cases, the regions 12 14 are already joined, and the stapling prevents/minimizes bleeding through the incision line so the region is simply a clamped region with a plurality of fasteners driven through the clamped tissue.

When the operative assembly 102 secures the tissue wall 4 in the closed position, the physician can inspect the secured structure to ensure that a region of healthy or base tissue 4 is adjacent to the fastening side/edge of the operative assembly 102. If the physician is uncertain or not satisfied, the jaw members can release the tissue and the physician can repeat the securing procedure.

Figure 8F:
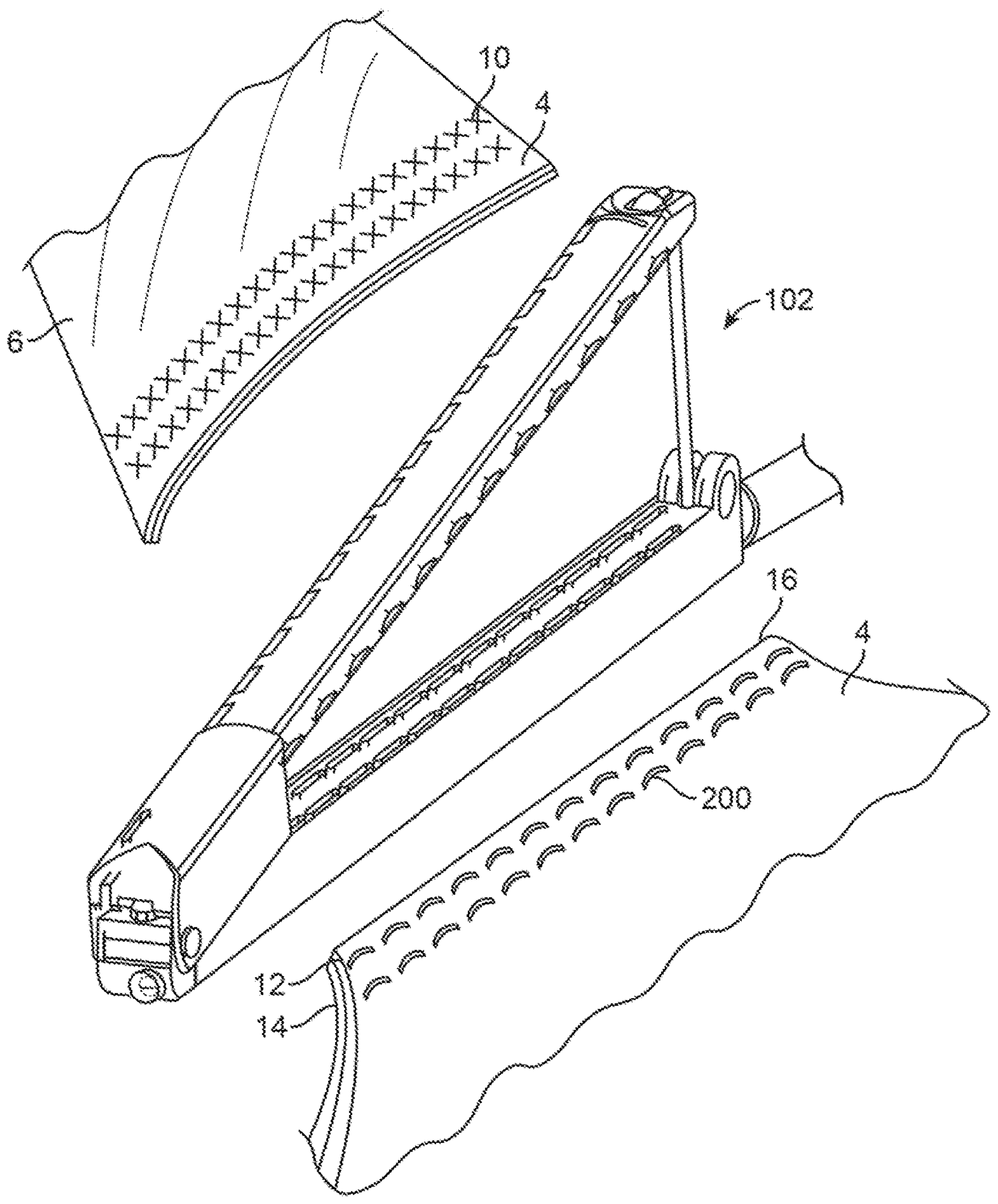

FIG. 8F illustrates the state of the procedure once the physician is satisfied with the margin of base tissue 4 and completes the cutting and fastening operations (in either order or simultaneously). FIG. 8F illustrates the operative assembly 102 in the open configuration with the joined region of tissue 16 (comprising fasteners 200 that secure the first region 12 and second region 14 of the wall 4 together). As noted above, the bounding of the operative site by the jaw members and boundary member ensures that the walls of the joined region of tissue are fully closed by the fasteners 200 and reduces the risk that an area of the joined region of tissue remains open to cause further patient complications.

In addition, the region of suspect tissue 6, its margin 10 and an adjacent region of base tissue 4 can be removed from the operative site. The device is then removed from the operative site.

Figure 9:
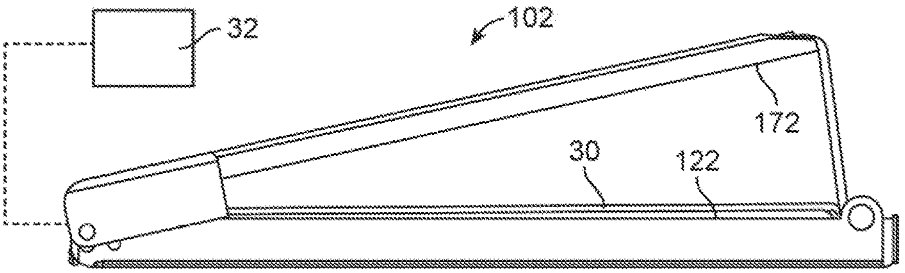
FIG. 9 illustrates an alternate variation of an operative assembly where the cutting element comprises an alternate type of cutting modality.

FIG. 9 illustrates an alternate variation of an operative assembly 102 where the cutting element comprises an element 30 that employs alternate modes to cut or otherwise treat the tissue, including but not limited to RF energy, resistive heat, ultrasound energy, plasma generated via a conductive fluid where the element 30 is coupleable to a power supply 32. Alternatively, or in combination, the power supply can be coupled to one or more conductive surfaces on the working surface 122 172 of the jaws to provide a coagulation source to prevent bleeding that might occur post procedure.

Figure 10A:
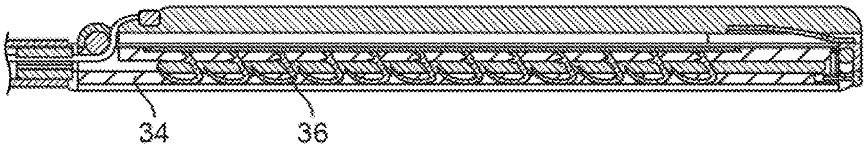
FIGS. 10A and 10B illustrate an example of a cartridge having a plurality of fasteners where the shaft and boundary member can be disengaged from the jaws.
Figure 10B:
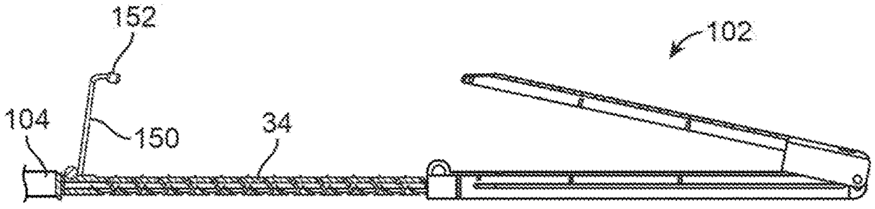

FIG. 10A illustrates one example of a cartridge 34 having a plurality of fasteners 36. Any number of fasteners can be used with the device, including but not limited to those described in U.S. Pat. No. 7,988,026, U.S. Pat. No. 8,403,956, U.S. Pat. No. 8,985,427, U.S. Pat. No. 9,004,339, U.S. Pat. No. 8,056,789, U.S. Pat. No. 8,631,992, U.S. Pat. No. 8,261,958, or U.S. Pat. No. 8,662,369. Variations of the devices include a single use operative assembly where the fasteners cannot be replaced. In some variations, a new set of fasteners can be placed on the device and be available for use. For example, the operative assembly 102 can be detached from the shaft 104 and distal end 152 of the link member 150 to permit reloading of one or more fastener cartridges 34 as shown in FIG. 10B.

FIGS. 11A-11F illustrate another variation of a surgical device where a cutting element is configured to maintain the clamping assembly in a closed position during the process of cutting tissue.

Figure 11A:
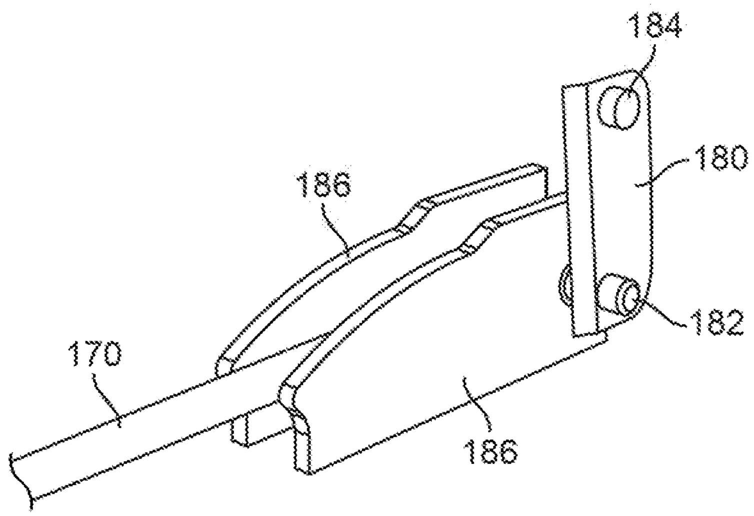
FIGS. 11A to 11F illustrate another variation of a surgical device where a cutting element is configured to maintain the clamping assembly in a closed position during the process of cutting tissue.

FIG. 11A illustrates one example of a cutting element 180 affixed to one or more wedges 186 that drive the staples or fasteners from a delivery configuration through the openings in the fastening track of the jaw assembly. As disclosed in the commonly assigned patents listed above, the wedges are shaped to first pivot the fasteners through tissue and then cause the fasteners to disengage from the cartridge. In the illustrated variation, an actuator member 170 actuates both the cutting element 180 and wedges 186 so that the fastening and cutting of the tissue occurs through the same actuation. By extending the surface of the wedge 186 proximal to the cutting element 180, fastening of tissue at a given location can occur immediately prior to cutting of the adjacent region of tissue. To ensure that the jaw assembly 102 remains closed and secures the tissue held therein during actuation, the cutting element 180 includes a first 182 and a second 184 extensions that slidably engage with the fixed jaw and second (actuating) jaw respectively. In the illustrated example, the extensions comprise pins, but any rigid structure can suffice as long as it allows slidable movement of the cutting element and while preventing separation of the jaws.

Figure 11B:
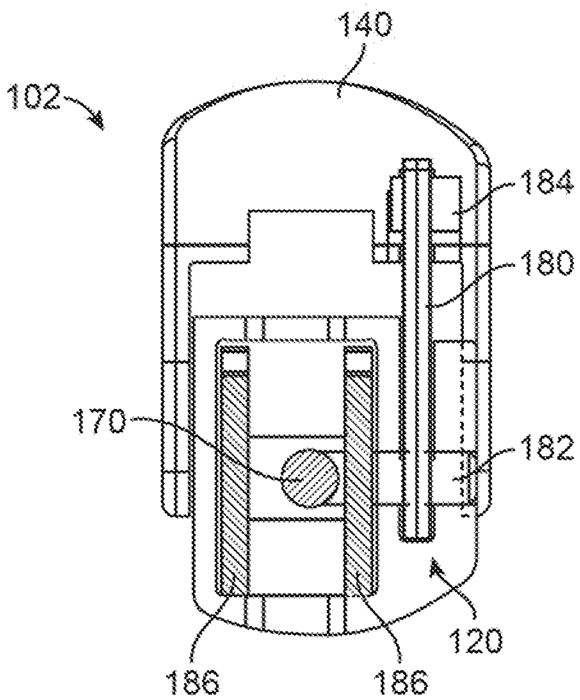
Figure 11C:
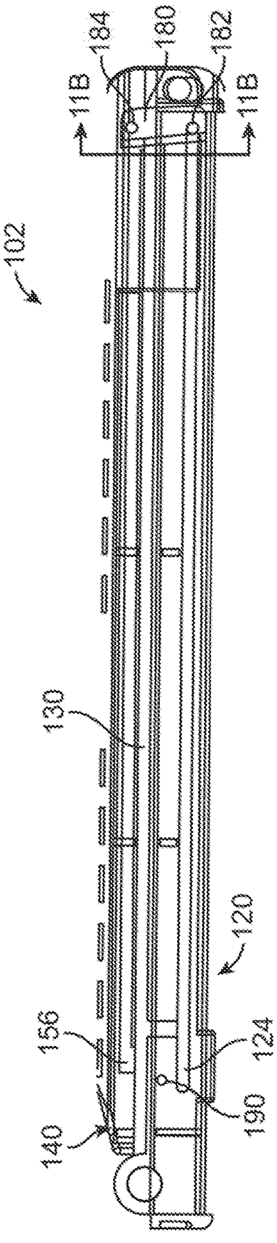

FIG. 11B illustrates a sectional view of the fixed jaw 120 and second (actuating) jaw 140 as taken along the lines 11B-11B of FIG. 11C. As illustrated, the first extension 182 engages a portion of the fixed jaw 120 while the second extension 184 engages a portion of the second jaw 140 such that the cutting element and respective extensions 182 and 184 mechanically engage the respective jaws during cutting of tissue to assist in maintaining the jaw surfaces clamped against the tissue. The extensions 184 and 182 extend laterally in both directions into grooves in the jaws as shown in FIG. 11B. The contact between the extensions 182 and 184 and grooves in the jaws holds the jaws tightly together at and near the point of cutting and fastening as the cutting element 180 and wedge 186 move along the jaws.

FIG. 11C illustrates a state of the jaw assembly 102 where the fixed 120 and actuating 140 jaws are in the closed position with a gap 130 therebetween. The cutting element 180 is located in a pre-deployment position, which in the illustrated variation is a distal most position. In this position, the first extension 182 is engaged within a slot or window 124 of the fixed jaw 120. The second extension 184 of the cutting element 180 is not yet engaged with the actuating jaw 140 in a manner that prohibits opening of the actuating jaw 140 relative to the fixed jaw 120. In FIG. 11C, the staples, cartridge, boundary member, and various other components are omitted for purposes of illustrating the cutting element 180 and engagement of the extensions 182, 184 with the jaw assembly.

Figure 11D:
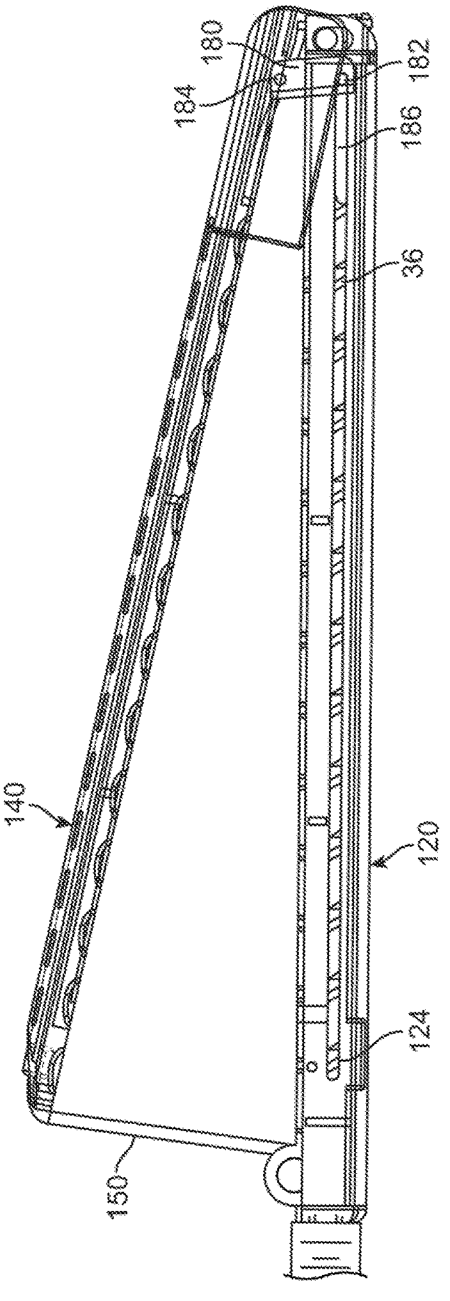

Accordingly, as shown in FIG. 11D, the second extension 184 does not prevent the actuating jaw 140 from opening as described above. In operation, the medical practitioner will open the jaw assembly with the cutting element in the pre-deployment position. Once the physician positions tissue appropriately within the jaw surfaces, the jaw assembly clamps the tissue so that the actuating member (not shown in FIG. 11D) can withdraw the wedges 186 which drive the fasteners 36 (partially visible through the slot or window 124) into tissue while the cutting element 180 severs tissue. Although the illustrated variation shows the cutting element as lagging to the wedges (and cuts a tissue region only after a fastener is driven into an adjacent region of tissue), variations of the device can include a cutting element leading, or even with the wedges.

Figure 11E:
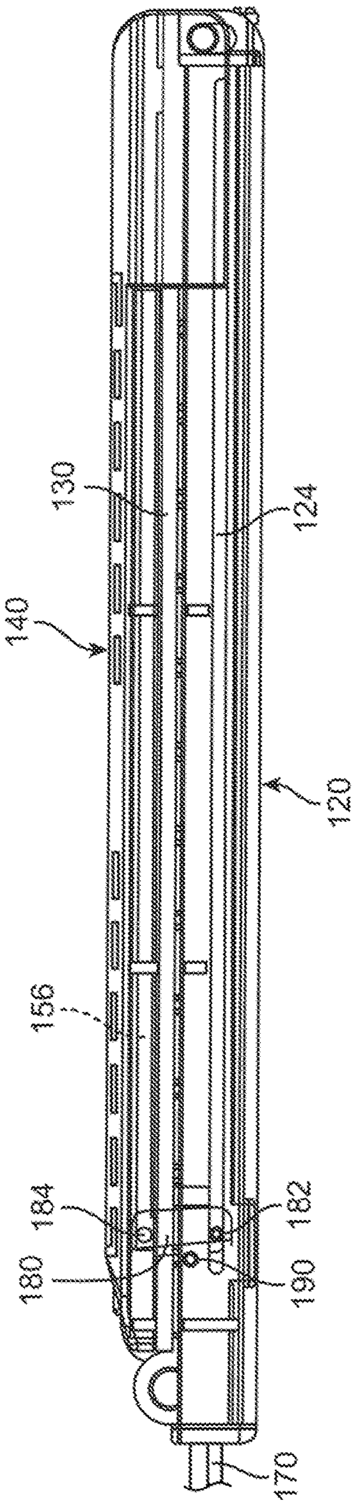
Figure 11F:
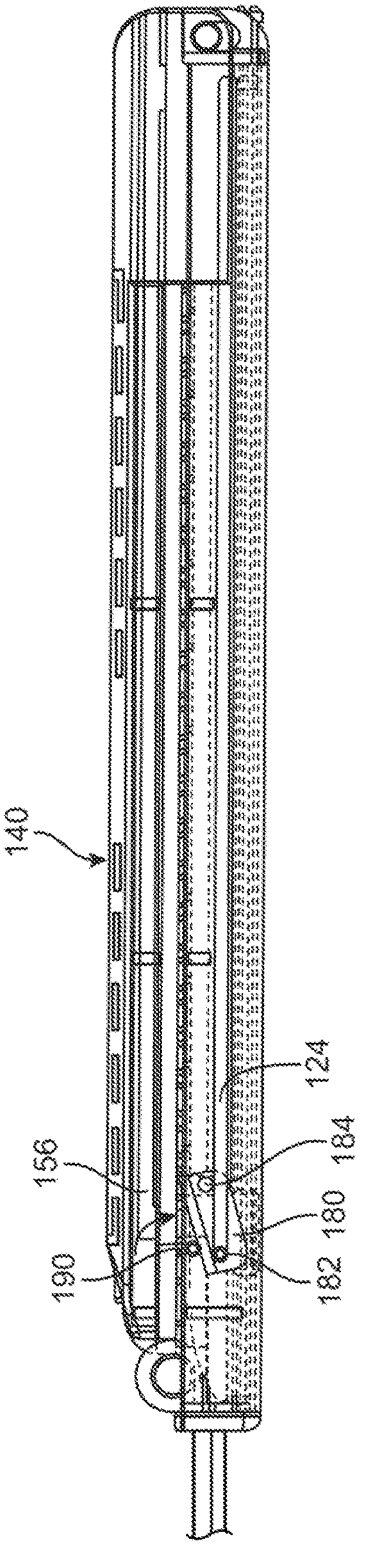

FIG. 11E illustrates the cutting element 180 at the end of the cutting stroke. As shown, the second extension 184 of the cutting element moves through the track 156 in the actuating jaw 140 to engage the actuating jaw 140 and prevent opening and maximizes compression of the actuating jaw 140 relative to the fixed jaw 120. As shown, the first extension 182 remains engaged within a slot 124 of the fixed jaw 120 during the cutting stroke. The illustrated variation of the device also shows a feature that prevents the need to retract the cutting element 180 to the pre-deployment position. Once the cutting element 180 reaches the end of the jaw assembly, cutting element 180 engages a pivot pin 190 that causes rotation of the cutting element 180 about the first extension 182 such that the second extension 184 disengages the actuating jaw 140. Once disengaged, the actuating jaw 140 can move relative to the fixed jaw to open and release the clamped tissue.

Figure 12A:
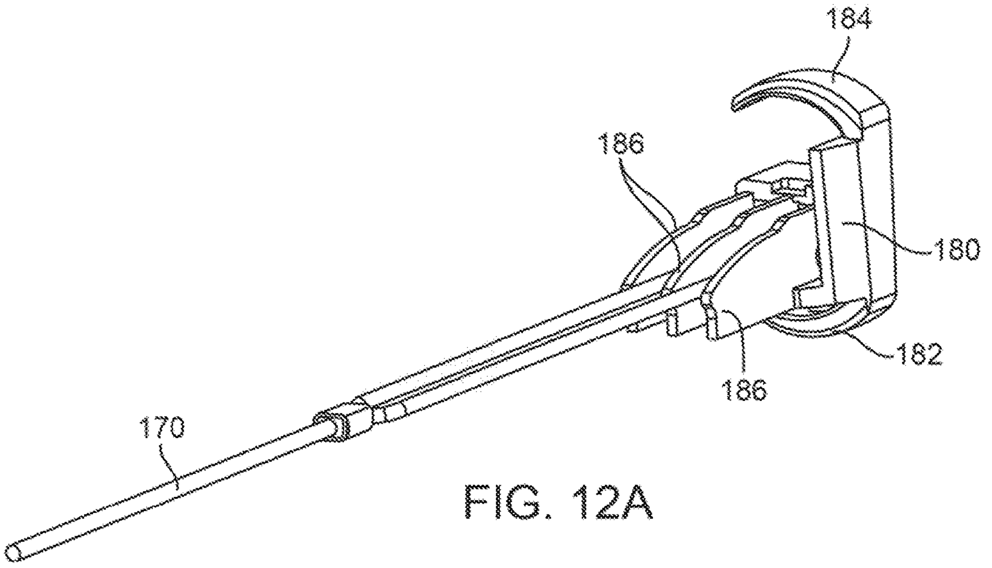
FIGS. 12A to 12F illustrate another variation of a surgical device where a cutting element is configured to maintain the clamping assembly in a closed position during the process of cutting tissue and the cutting assembly moves over an exterior surface of the device.

FIGS. 12A-12F illustrate another variation of a device as described herein. FIG. 12A illustrates a variation of a cutting element 180 affixed to three wedges 186 where the number of wedges corresponds to the number of fastening tracks or fastener lines in the device. While the variations illustrated in this document include 2 or 3 lines, any number of lines of fasteners are within the scope of the disclosure. The wedges 186 and cutting element can be pulled by a single actuator member 170 or multiple boundary members to allow for separate actuation of various components. In the illustrated example, the actuator member 170 bifurcates to provide an even pulling force on the wedge/cutting assembly.

Figure 12B:
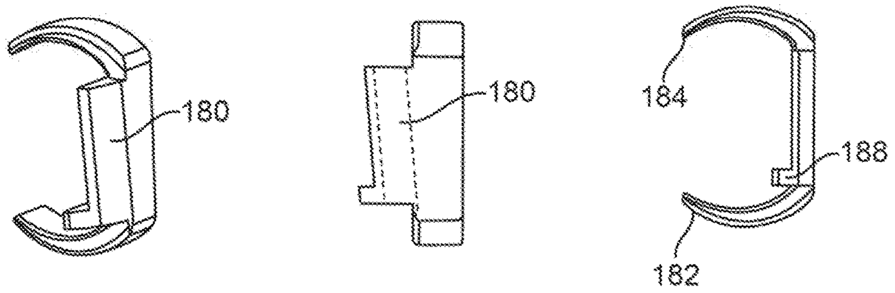

The cutting element 180 illustrates in FIG. 12A is configured to translate along an exterior side of the jaw assembly (as discussed below). However, the cutting element 180 can also include a first extension 182 and a second extension 184 to maintain closure of the jaws as the cutting element 180 moves along the jaws to cut tissue. FIG. 12B illustrates a perspective, side, and front view of the cutting element 180 and extensions 182, 184. As discussed below, the extensions engage an exterior surface of the jaw assembly and can be shaped to match a profile of the exterior surface of the jaws. In addition, the cutting element 180 can include a key 188 that engages the fixed jaw and allow for securing of the cutting element 180 to the wedge assembly as discussed in FIGS. 12D and 12E.

Figure 12C:
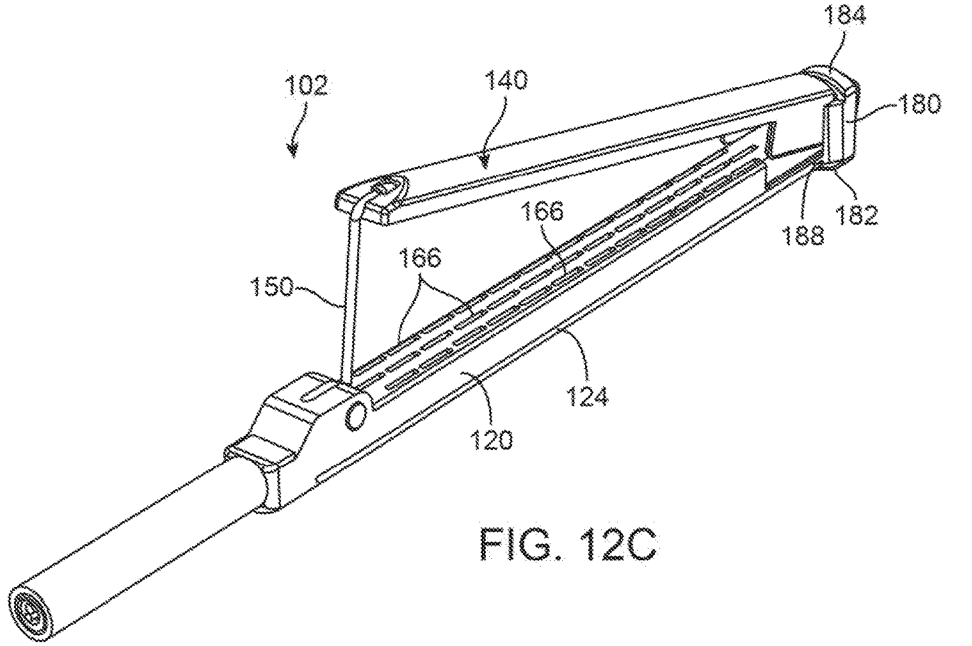

FIG. 12C illustrates the cutting element 180 of FIGS. 12A and 12B on a surgical device 102. As shown, the cutting element 180 is in a pre-deployment configuration that is located at a distal end of the jaw assembly. As such, the cutting element 180 and first extension 182 remain engaged within the fixed jaw 120 through the key 188 that extends through the slot 124 of the fixed jaw 120. However, the second extension 184 is configured such that the actuating jaw 140 can move to an open configuration. In certain variations, the second extension 184 engages the actuating jaw 140 but to an extent that allows for opening of the jaw when the cutting element 180 is in the pre-deployment configuration. For example, in the variation shown in FIG. 12C, the actuating jaw 140 includes a recess 188 (shown in FIG. 12D) that permits movement of the jaw. FIG. 12C also illustrates three cutting tracks 166 along a working surface of the fixed jaw 120.

Figure 12D:
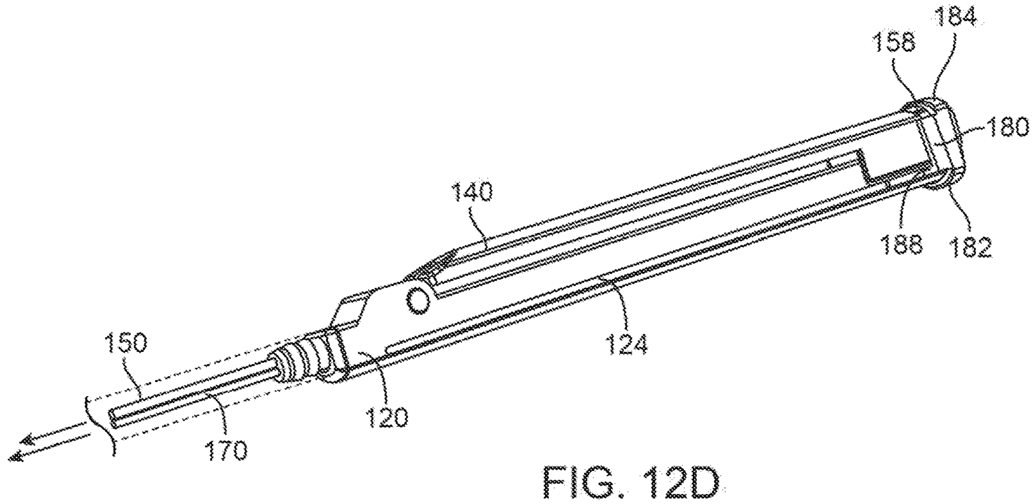

FIG. 12D illustrates the fixed 120 and actuating 140 jaws in the closed position via application of a force applied by the boundary member 150. The actuator member 170 can then apply a force to move the cutting element 180 longa side of the jaw assembly, where the key 188 of the cutting element 180 remains engaged with the fixed jaw 120 through a slot 124 and where the first extension 182 remains engaged the fixed jaw 120 as it slides along an outer surface of the fixed jaw. The second extension 184 does not engage (or prevent movement of) the second jaw 140 until it passes the recess 158 in the second jaw 140. Accordingly, once the cutting element 180 moves proximally along the jaw assembly, the second extension 184 engages the second jaw 140 as it slides along an outer surface of the second jaw 140. Likewise, the cutting element 180 moves along an exterior side or lateral surface of the jaws. Therefore, as shown in FIG. 12C, this variation of the device does not include a cutting track on the jaw surface. <*clean this up*>

Figure 12E:
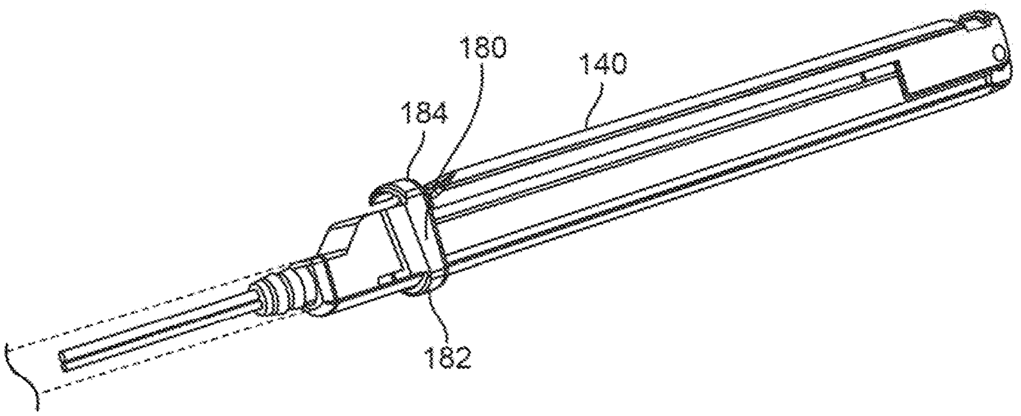
Figure 12F:
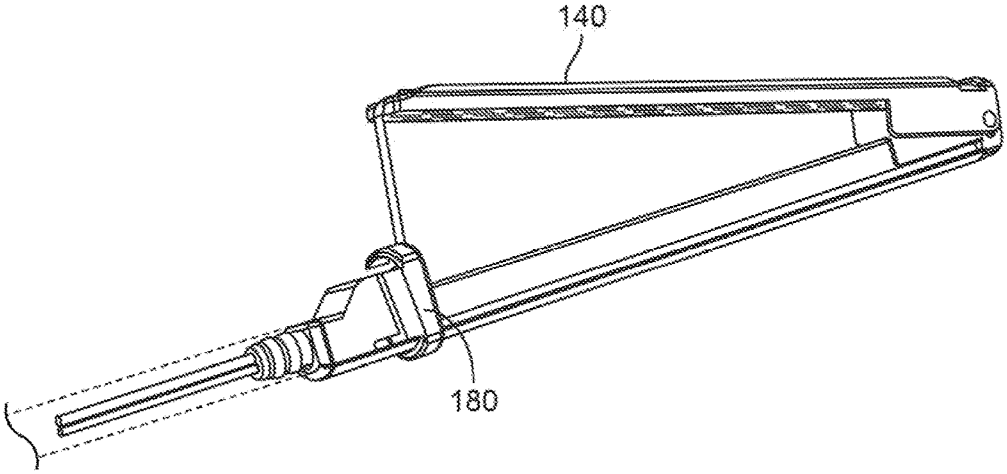

FIG. 12E shows the cutting element 180 in a proximal or post deployment configuration, where the second extension 184 disengages the second jaw 140. Accordingly, the second jaw 140 can be moved into an open configuration, as shown in FIG. 12F, without movement of the cutting element 180 back to the pre-deployment configuration to the opposite end of the jaws.

Figure 13A:
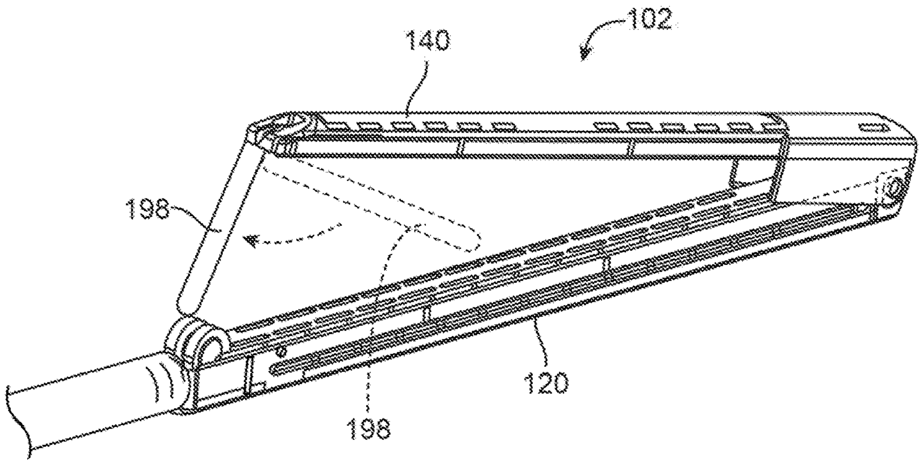
FIGS. 13A to 13D show a variation of the device with a boundary member that is coupled to a single jaw member.
Figure 13B:
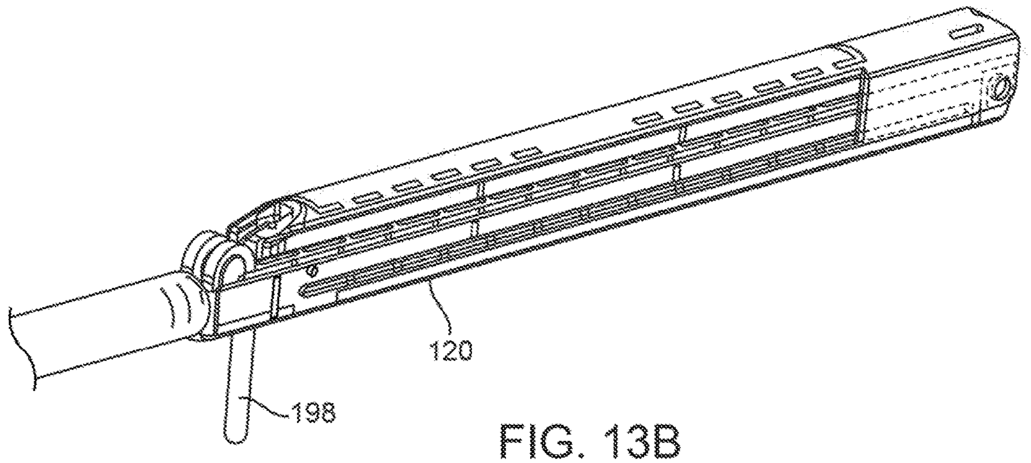

FIGS. 13A to 13D show an alternate example of a device having a boundary member 198 coupled to only one jaw member. In this variation, the boundary member 198 comprises an arm-like structure that is offset on the jaw assembly to allow pivoting to form a closed boundary. FIG. 13A shows a variation of a device 102 where the boundary member 198 is deployable from an actuating jaw 140. As discussed above, the device 102 can be deployed with a minimum profile, where the boundary member 198 extends along a side or along a jaw surface of the actuating jaw 140. Once the jaw opens, the physician can deploy the boundary member 198 to provide a barrier at the open side of the jaws. When the jaw is closed, as shown in FIG. 13B, the boundary member 198 can extend beyond the fixed jaw 120 or can be retracted to the actuating jaw.

Figure 13C:
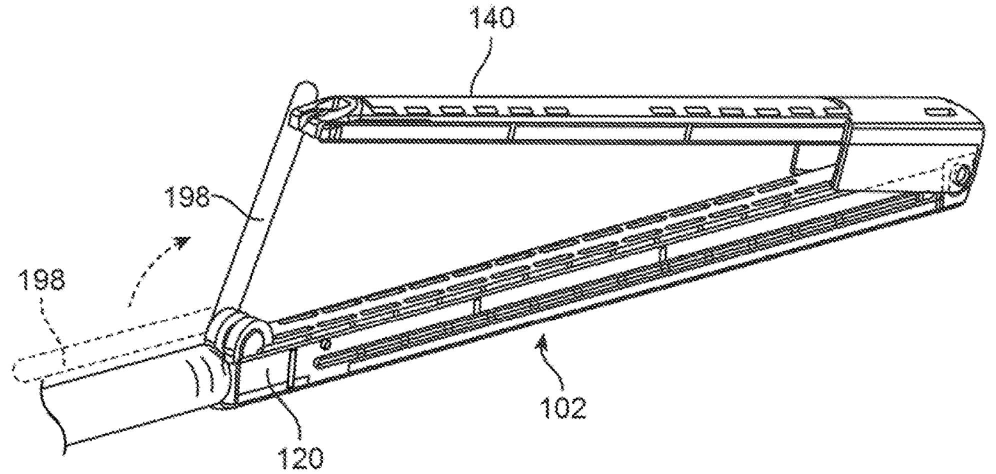
Figure 13D:
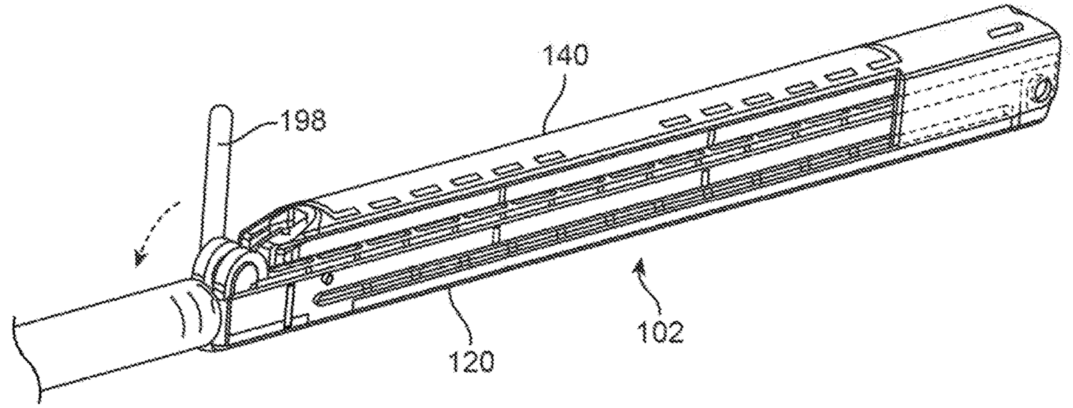

FIG. 13C illustrates a boundary member 198 that is coupled to the fixed jaw 120. As noted above, the boundary member 198 can be actuated at any time to provide a barrier towards the non-pivoting of the jaws. When the jaws are closed and the procedure completed, the boundary member 198 can be retracted back to the pre-deployment configuration.

Figure 14:
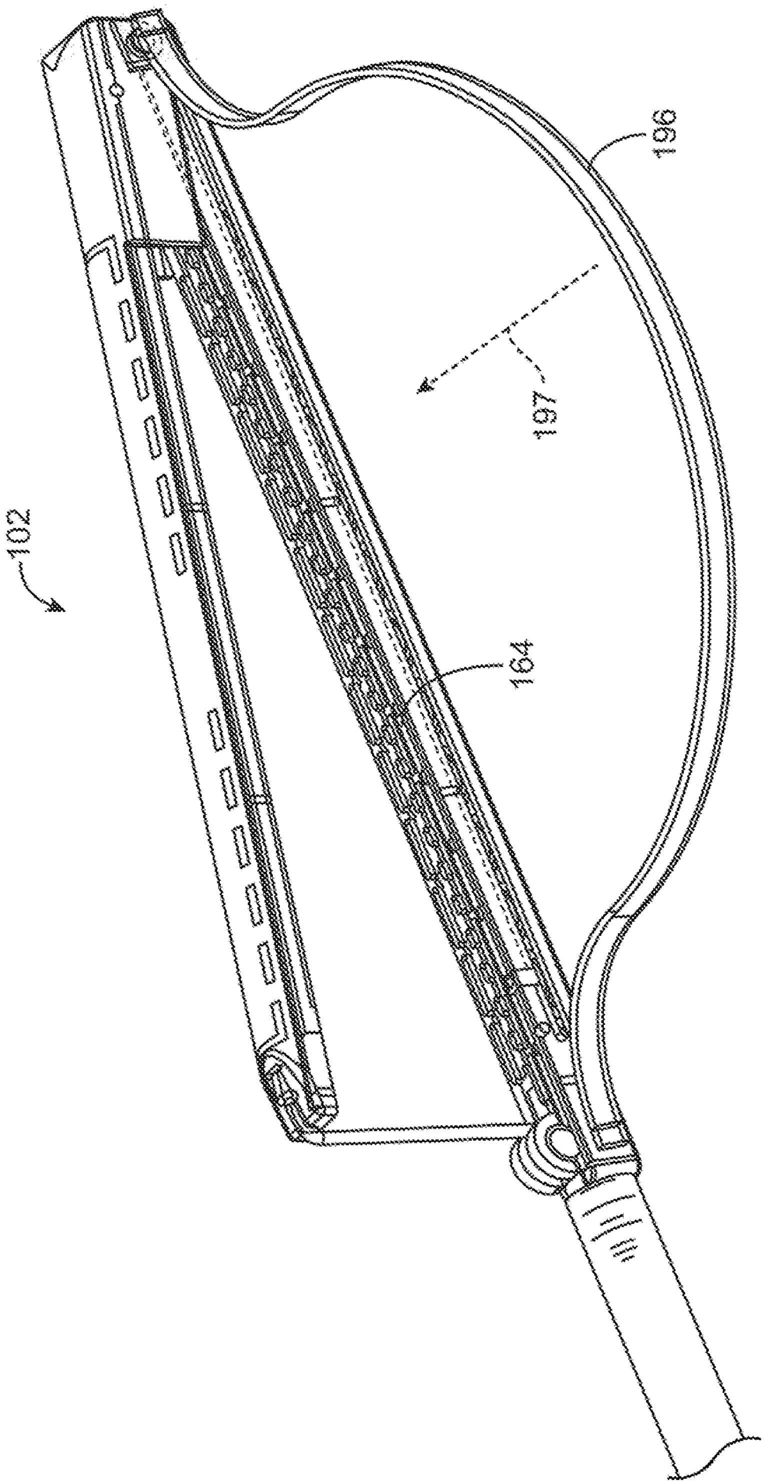
FIG. 14 illustrates a positioning loop used in addition to the surgical assembly.

FIG. 14 shows a variation of a device 102 having a positioning loop 196 extending to a side of the device. Typically, the positioning loop extends from a side of the device adjacent to the cutting track 164. However, alternate variations include a positioning loop adjacent to the opposite side of the device. The positioning loop 196 can be configured to be permanently bowed away from the jaw assembly. Alternatively, it can be configured to retract towards the jaw assembly (as shown by arrow 197) when desired.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A surgical device for separating a region of tissue from a tissue structure and for use with a plurality of fasteners, the surgical device comprising:

a shaft;

a first jaw located at an end of the shaft, the first jaw having a first end and a second end and a working surface that extends along a length of the first jaw between the first end and the second end;

a second jaw being coupled to the first jaw at the first end to allow the second jaw to move relative to the first jaw between an open position and a closed position;

a boundary member operatively coupling the second jaw to the first jaw at the second end such that a distal end of the boundary member moves with the second jaw between the open and closed position while remaining engaged with to the first jaw, wherein application of a tensile force on the boundary member retracts the boundary member to pull the second jaw towards the closed position;

a fastening track comprising a plurality of fastening openings located on the working surface to permit movement of the plurality of fasteners therethrough, the fastening track being adjacent to a first edge of the first jaw to permit movement of the fasteners therethrough;

a cutting track adjacent to a second edge of the first jaw; and a cutting element moveable along the cutting track, where actuation of the cutting element causes movement of the cutting element along the cutting tract; and a first extension of the cutting element being slidably coupled to a portion of the first jaw and a second extension of the cutting element slidably coupled to a portion of the second jaw, such that as the cutting element moves along the cutting track, the portion of the first jaw and the portion of the second jaw prevents the second jaw from moving away from the first jaw, where the second extension disengages from the second jaw to permit opening of the second jaw relative to the first jaw when the cutting element is in a distal position along the first jaw and when the cutting element is in a proximal position along the first jaw.

2. The surgical device of claim 1, where the first jaw is fixed at the end of the shaft such that the second jaw moves and the first jaw remains stationary when actuated.

3. The surgical device of claim 1, wherein the boundary member is configured to advance away from the first jaw when the second jaw is in the open position such that the distal end of the boundary member remains coupled to the second jaw and a portion of the boundary member expands away from the first jaw to an extended profile, where the extended profile permits capturing of the tissue structure beyond the working surface when the second jaw is in the open position, and where proximal movement of the boundary member direct the tissue structure towards the working surface as the second jaw assumes the closed position.

4. The surgical device of claim 1, wherein the boundary member is releasably coupled to the second jaw to permit detachment of the first and second jaw from the shaft, and further comprising a cartridge containing the plurality of fasteners.

5. The surgical device of claim 1, wherein the second jaw is spring biased to the open position.

6. The surgical device of claim 1, wherein the cutting track spans beyond the fastening track on the first and second end of the first jaw.

7. The surgical device of claim 1, wherein the cutting element comprises a blade.

8. The surgical device of claim 1, wherein the cutting element comprises an electrosurgical cutting apparatus.

9. The surgical device of claim 1, wherein the fastening track comprises at least two parallel rows of the plurality of fastening openings.

10. The surgical device of claim 1, wherein the second end of the first jaw is adjacent to the shaft such that the first end of the first jaw comprises a distal end of the surgical device.

11. The surgical device of claim 1, wherein the shaft comprises a flexible shaft.

12. The surgical device of claim 1, further comprising a handle having an actuator.

13. The surgical device of claim 12, wherein the actuator is coupled to the boundary member and configured to actuate the boundary member.

14. The surgical device of claim 12, wherein the actuator is coupled to the cutting element and configured to actuate the cutting element.

15. The surgical device of claim 1, wherein the boundary member extends through the shaft.

16. The surgical device of claim 1, wherein the fastening track and cutting track are parallel along the first jaw.

17. The surgical device of claim 1, wherein the cutting element is positioned to cut tissue during movement in a proximal direction.

18. The surgical device of claim 1, wherein the first end of the first jaw is located distally of the second end of the first jaw.

19. The surgical device of claim 1, wherein the boundary member is configured to be moved distally to assume an expanded profile when coupled to the second jaw and the first jaw.

20. The surgical device of claim 1, where the operatively coupling of boundary member to the first jaw and second jaw also forms a mechanical barrier at the second end that prevents the tissue structure from extending in a longitudinal direction beyond the working surface when the tissue structure is positioned transversely across the working surface between the first jaw and second jaw when the second jaw is in the closed position.

* * * * *